United States Patent
Song et al.

(10) Patent No.: US 7,501,179 B2
(45) Date of Patent: Mar. 10, 2009

(54) BLOCK COPOLYMER PARTICLES

(75) Inventors: Young-Ho Song, Natick, MA (US); Eric D. Welch, Miramar, FL (US); Scott T. Bluni, Sudbury, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 53 days.

(21) Appl. No.: 11/314,557

(22) Filed: Dec. 21, 2005

(65) Prior Publication Data

US 2007/0141339 A1  Jun. 21, 2007

(51) Int. Cl.
 B32B 5/66  (2006.01)
(52) U.S. Cl. ............... 428/402; 428/403; 428/404; 428/405; 428/406; 428/407; 428/522
(58) Field of Classification Search ............. 428/402, 428/403, 404, 405, 406, 407, 522
See application file for complete search history.

(56) References Cited

U.S. PATENT DOCUMENTS

| | | |
|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,276,394 A | 6/1981 | Kennedy et al. |
| 4,316,973 A | 2/1982 | Kennedy |
| 4,342,849 A | 8/1982 | Kennedy |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,671,994 A | 6/1987 | Cochran, Jr. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,708,930 A | 11/1987 | Kortright et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |

(Continued)

FOREIGN PATENT DOCUMENTS

| | | |
|---|---|---|
| AU | A-76186/98 | 10/1998 |
| CN | 1273860 | 11/2000 |
| DE | 3834705 | 4/1990 |
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |

(Continued)

OTHER PUBLICATIONS

U.S. Appl. No. 11/117,156, filed Apr. 28, 2005, Lanphere et al.
U.S. Appl. No. 11/124,828, filed May 9, 2005, McIntyre et al.
U.S. Appl. No. 11/125,297, filed May 9, 2005, Li et al.
U.S. Appl. No. 11/154,106, filed Jun. 15, 2005, Tan.
U.S. Appl. No. 11/165,949, filed Jun. 24, 2005, Tan.
U.S. Appl. No. 11/184,223, filed Jul. 19, 2005, Richard et al.
U.S. Appl. No. 11/248,033, filed Oct. 12, 2005, Buiser et al.
U.S. Appl. No. 11/248,493, filed Oct. 12, 2005, Buiser et al.
U.S. Appl. No. 11/274,538, filed Nov. 15, 2005, Tenney et al.
U.S. Appl. No. 11/311,617, filed Dec. 19, 2005, Buiser et al.

(Continued)

*Primary Examiner*—Leszek Kiliman
(74) *Attorney, Agent, or Firm*—Fish & Richardson P.C.

(57) ABSTRACT

Block copolymer particles, and related compositions and methods, are disclosed.

35 Claims, 32 Drawing Sheets

U.S. PATENT DOCUMENTS

| | | | |
|---|---|---|---|
| 4,795,741 A | 1/1989 | Leshchiner et al. |
| 4,801,458 A | 1/1989 | Hidaka et al. |
| 4,804,366 A | 2/1989 | Zdeb et al. |
| 4,815,737 A | 3/1989 | Su et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,910,321 A | 3/1990 | Kennedy et al. |
| 4,929,400 A | 5/1990 | Rembaum et al. |
| 4,929,683 A | 5/1990 | Kennedy et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,066,730 A | 11/1991 | Kennedy et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,122,572 A | 6/1992 | Kennedy et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,574 A | 11/1995 | Ehrenberg et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |

| | | |
|---|---|---|
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |
| 5,895,411 A | 4/1999 | Irie |
| 5,899,877 A | 5/1999 | Leibitzki et al. |
| 5,902,832 A | 5/1999 | Van Bladel et al. |
| 5,902,834 A | 5/1999 | Porrvik |
| 5,922,025 A | 7/1999 | Hubbard |
| 5,922,304 A | 7/1999 | Unger |
| 5,922,676 A | 7/1999 | Pasqualini et al. |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 6,003,566 A | 12/1999 | Thibault et al. |
| 6,015,546 A | 1/2000 | Sutton et al. |
| 6,027,472 A | 2/2000 | Kriesel et al. |
| 6,028,066 A | 2/2000 | Unger |
| 6,047,861 A | 4/2000 | Vidal et al. |
| 6,048,908 A | 4/2000 | Kitagawa |
| 6,051,247 A | 4/2000 | Hench et al. |
| 6,056,721 A | 5/2000 | Shulze |
| 6,056,844 A | 5/2000 | Guiles et al. |
| 6,059,766 A | 5/2000 | Greff |
| 6,063,068 A | 5/2000 | Fowles et al. |
| 6,068,829 A | 5/2000 | Ruoslahti et al. |
| 6,071,495 A | 6/2000 | Unger et al. |
| 6,071,497 A | 6/2000 | Steiner et al. |
| 6,072,004 A | 6/2000 | Migchels et al. |
| 6,073,759 A | 6/2000 | Lamborne et al. |
| 6,090,925 A | 7/2000 | Woiszwillo et al. |
| 6,096,344 A | 8/2000 | Liu et al. |
| 6,099,864 A | 8/2000 | Morrison et al. |
| 6,100,306 A | 8/2000 | Li et al. |
| 6,139,963 A | 10/2000 | Fujii et al. |
| 6,149,623 A | 11/2000 | Reynolds |
| 6,160,084 A | 12/2000 | Langer et al. |
| 6,162,377 A | 12/2000 | Ghosh et al. |
| 6,165,193 A | 12/2000 | Greene, Jr. et al. |
| 6,165,440 A | 12/2000 | Esenaliev |
| 6,179,817 B1 | 1/2001 | Zhong |
| 6,191,193 B1 | 2/2001 | Lee et al. |
| 6,214,331 B1 | 4/2001 | Vanderhoff et al. |
| 6,214,384 B1 | 4/2001 | Pallado et al. |
| 6,224,630 B1 | 5/2001 | Bao et al. |
| 6,224,794 B1 | 5/2001 | Amsden et al. |
| 6,235,224 B1 | 5/2001 | Mathiowitz et al. |
| 6,238,403 B1 | 5/2001 | Greene, Jr. et al. |
| 6,245,090 B1 | 6/2001 | Gilson et al. |
| 6,251,661 B1 | 6/2001 | Urabe et al. |
| 6,258,338 B1 | 7/2001 | Gray |
| 6,261,585 B1 | 7/2001 | Sefton et al. |
| 6,264,861 B1 | 7/2001 | Tavernier et al. |
| 6,267,154 B1 | 7/2001 | Felicelli et al. |
| 6,268,053 B1 | 7/2001 | Woiszwillo et al. |
| 6,277,392 B1 | 8/2001 | Klein |
| 6,280,457 B1 | 8/2001 | Wallace et al. |
| 6,291,605 B1 | 9/2001 | Freeman et al. |
| 6,296,604 B1 | 10/2001 | Garibaldi et al. |
| 6,296,622 B1 | 10/2001 | Kurz et al. |
| 6,296,632 B1 | 10/2001 | Luscher et al. |
| 6,306,418 B1 | 10/2001 | Bley |
| 6,306,419 B1 | 10/2001 | Vachon et al. |
| 6,306,425 B1 | 10/2001 | Tice et al. |
| 6,306,427 B1 | 10/2001 | Annonier et al. |
| 6,312,407 B1 | 11/2001 | Zadno-Azizi et al. |
| 6,312,942 B1 | 11/2001 | Plüss-Wenzinger et al. |
| 6,315,709 B1 | 11/2001 | Garibaldi et al. |
| 6,335,384 B1 | 1/2002 | Evans et al. |
| 6,344,182 B1 | 2/2002 | Sutton et al. |
| 6,355,275 B1 | 3/2002 | Klein |
| 6,368,658 B1 | 4/2002 | Schwarz et al. |
| 6,379,373 B1 | 4/2002 | Sawhney et al. |
| 6,388,043 B1 | 5/2002 | Langer et al. |
| 6,394,965 B1 | 5/2002 | Klein |
| 6,410,508 B1 | 6/2002 | Isales et al. |
| 6,423,332 B1 | 7/2002 | Huxel et al. |
| 6,432,437 B1 | 8/2002 | Hubbard |
| 6,436,112 B2 | 8/2002 | Wensel et al. |
| 6,443,941 B1 | 9/2002 | Slepian et al. |
| 6,458,296 B1 | 10/2002 | Heinzen et al. |
| 6,476,069 B2 | 11/2002 | Krall et al. |
| 6,495,155 B1 | 12/2002 | Tice et al. |
| 6,527,716 B1 | 3/2003 | Eppstein |
| 6,544,503 B1 | 4/2003 | Vanderhoff et al. |
| 6,544,544 B2 | 4/2003 | Hunter et al. |
| 6,545,097 B2 | 4/2003 | Pinchuk et al. |
| 6,575,896 B2 | 6/2003 | Silverman et al. |
| 6,586,364 B2 | 7/2003 | Kubota et al. |
| 6,602,261 B2 | 8/2003 | Greene, Jr. et al. |
| 6,602,524 B2 | 8/2003 | Batich et al. |
| 6,605,111 B2 | 8/2003 | Bose et al. |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,680,046 B1 | 1/2004 | Boschetti |
| 6,699,222 B1 | 3/2004 | Jones et al. |
| 6,949,112 B1 | 9/2005 | Sridharan et al. |
| 6,998,137 B2 * | 2/2006 | Shih et al. .................. 424/426 |
| 7,053,134 B2 | 5/2006 | Baldwin et al. |
| 7,094,369 B2 | 8/2006 | Buiser et al. |
| 2001/0001835 A1 | 5/2001 | Greene, Jr. et al. |
| 2001/0016210 A1 | 8/2001 | Mathiowitz et al. |
| 2001/0036451 A1 | 11/2001 | Goupil et al. |
| 2001/0051670 A1 | 12/2001 | Goupil et al. |
| 2002/0054912 A1 | 5/2002 | Kim et al. |
| 2002/0061954 A1 | 5/2002 | Davis et al. |
| 2002/0138154 A1 | 9/2002 | Li et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0091556 A1 | 5/2003 | Ruoslahti et al. |
| 2003/0108614 A1 | 6/2003 | Volkonsky et al. |
| 2003/0113320 A1 | 6/2003 | Ruoslahti et al. |
| 2003/0185895 A1 | 10/2003 | Lanphere et al. |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0206864 A1 | 11/2003 | Mangin |
| 2003/0215519 A1 | 11/2003 | Schwarz et al. |
| 2003/0233150 A1 | 12/2003 | Bourne et al. |
| 2004/0076582 A1 | 4/2004 | DiMatteo et al. |
| 2004/0091543 A1 | 5/2004 | Bell et al. |
| 2004/0092883 A1 | 5/2004 | Casey, III et al. |
| 2004/0096662 A1 | 5/2004 | Lanphere et al. |
| 2004/0101564 A1 | 5/2004 | Rioux et al. |
| 2004/0186377 A1 | 9/2004 | Zhong et al. |
| 2005/0025800 A1 | 2/2005 | Tan |

| | | | | | | |
|---|---|---|---|---|---|---|
| 2005/0037047 | A1 | 2/2005 | Song | WO | WO 00/66183 | 11/2000 |
| 2005/0095428 | A1 | 5/2005 | DiCarlo et al. | WO | WO 00/71196 | 11/2000 |
| 2005/0129775 | A1 | 6/2005 | Lanphere et al. | WO | WO 00/74633 | 12/2000 |
| 2005/0196449 | A1 | 9/2005 | DiCarlo et al. | WO | WO 01/12359 | 2/2001 |
| 2005/0208107 | A1 | 9/2005 | Helmus et al. | WO | WO 01/66016 | 9/2001 |
| 2005/0226935 | A1 | 10/2005 | Kamath et al. | WO | WO 01/70291 | 9/2001 |
| 2005/0238870 | A1 | 10/2005 | Buiser et al. | WO | WO 01/72281 | 10/2001 |
| 2005/0263916 | A1 | 12/2005 | Lanphere et al. | WO | WO 01/76845 | 10/2001 |
| 2006/0013849 | A1 | 1/2006 | Strickler et al. | WO | WO 01/93920 | 12/2001 |
| 2006/0045900 | A1 | 3/2006 | Richard et al. | WO | WO 02/11696 | 2/2002 |
| 2006/0100568 | A1 | 5/2006 | Tan | WO | WO 02/34298 | 5/2002 |
| 2006/0116711 | A1 | 6/2006 | Elliott et al. | WO | WO 02/34299 | 5/2002 |
| 2006/0165753 | A1 | 7/2006 | Richard | WO | WO 02/34300 | 5/2002 |
| 2006/0171985 | A1 | 8/2006 | Richard et al. | WO | WO 02/43580 | 6/2002 |
| 2006/0199009 | A1 | 9/2006 | Anderson et al. | WO | WO02/47731 * | 6/2002 |
| 2006/0199010 | A1 | 9/2006 | DiCarlo et al. | WO | WO 02/47731 | 6/2002 |

FOREIGN PATENT DOCUMENTS

| | | |
|---|---|---|
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| EP | 1 498 455 | 1/2005 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/40631 | 7/2000 |
| WO | WO 03/013552 | 2/2003 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/040972 | 5/2004 |
| WO | WO 2004/073688 | 9/2004 |
| WO | WO 2004/075989 | 9/2004 |
| WO | WO 2005/057272 | 6/2005 |

OTHER PUBLICATIONS

U.S. Appl. No. 11/314,056, filed Dec. 21, 2005, Song et al.

Abbara et al., "Transcervical Expulsion of a Fibroid as a Result of Uterine Artery Embolization for Leiomyomata", *JVIR*, vol. 10, No. 4, pp. 409-411, 1999.

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Ahuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Armeanu et al., "In vivo perivascular implantation of encapsulated packaging cells for prolonged retroviral gene transfer," *J. Microencapsulation*, 18(4):491-506 (2001).

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D., et al., "Polyvinyl Alcohol Foam Particles Sizes and Concentrations Injectable through Microcatheters", *JVIR*, vol. 9, No. 1, pp. 113-118; 1998.

Barton, P. et al., "Embolization of Bone Metastases," *Journal of Vascular and Interventional Radiology*, 7(1):81-88 (Jan.-Feb. 1996).

Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bilbao et al., "A blood-tumor barrier limits gene transfer to experimental liver cancer: the effect of vasoactive compounds," *Gene Ther.*, 7:1824-1832 (2000).

Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. El, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (English Summary included).

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~moreland/stats/hcc-9.html.

Concentric Medical, Inc.- Product Information (3 pages), 2002.

Cruise et al., "In Vitro and In Vivo Characterization of a Hydrogel-Based Aneurysm Embolization System," *Society for Biomaterials 28th Annual Meeting Transactions*, p. 203 (2002).

Deasy, P. B., "Microencapsulation and Related Drug Processes", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

George, "Modeling the Melt Spinning Process," *Polymers for Fibers and Elastomers*, Chapter 23, pp. 355-369 (1984).

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No, 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*, 17:1901-1906 (Nov. 1996).

Hirano et al., "Transcutaneous Intrafold Injection For Unilateral Vocal Fold Paralysis: Functional Results," *Ann. Otol. Rhinol Laryngol.*, 99(8):598-604 (Aug. 1990).

Horak et al., "Hydrogels in endovascular embolization. I. Spherical particles of poly (2-hydroxyethyl methacrylate) and their medicobiological properties", *Biomaterials*, 7(3):188-192 (May 1986).

Horak et al., "Hydrogels in endovascular embolization. II. Clinical use of spherical particles", *Biomaterials*, 7(6):467-470 (Nov. 1986).

Hori et al., "Management of peripheral AVMs by embolotherapy using SAP-microsphere," *European Congress of Radiology*, Abstract 1024, http://www.ecr.org/conferences/ecr1997/sciprg/abs/9701024o.htm, 1 page (Retrieved from the Internet on Dec. 2, 2003).

Huang et al., "Hydrophilic-hydrophobic biodegradable polymers: release characteristics of hydrogen-bonded, ring-containing polymer matrices," *Biomaterials*, 15(15):1243-1247 (1994).

Huang et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (English Abstract included).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim et al., "Composite poly(vinyl alcohol) beads for controlled drug delivery", *Pharm Res*, vol. 9. No. 1, pp. 10-16, 1992.

Kim et al., "Hollow Silica Spheres of Controlled Size and Porosity by Sol-Gel Processing," *J. Am. Ceram. Soc.*, 74(8):1987-1992 (Aug. 1991).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992 (English Abstract included).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (English Abstract included).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Kwon et al., "Arborescent Polyisobutylene-Polystyrene Block Copolymers-A New Class of Thermoplastic Elastomers," *Polymer Preprints*, 43(1):266 (Spring 2002).

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (English Abstract included).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

"Lecture 5: Controlled Release Devices," BEH.462/3.962J Molecular Principles of Biomaterials, 14 pages (Spring 2003).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

"Matrix® Detachable Coils," Boston Scientific, http://www.bostonscientific.com, 3 pages (retrieved from the Internet on Jul. 13, 2005).

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Minamitani et al., "Embolization therapy of neoplastic lesions using a new embolic material without antineoplastic agents," *European Congress of Radiology*, Abstract 1499, http://www.ecr.org/conferences/ecr1997/sciprg/abs/9701499o.htm, 1 page (Retrieved from the Internet on Dec. 2, 2003).

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Nam et al., "A Novel Fabrication Method of Macroporous Biodegradable Polymer Scaffolds Using Gas Foaming Salt as a Porogen Additive," *J. Biomed. Mater. Res. (Appl. Biomater.)*, 53:1-7 (2000).

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization," http://www.uhmc.edu/dotter-fibroid, 34 pages.

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Pardridge et al., "Therapeutic Targeting, Blood-Brain Barrier, Gene Therapy, and Vascular Biology," National Institute of Neurological Disorders and Stroke, http://www.ninds.nih.gov/find_people/groups/brain_tumor_prg/therapeutictargeting_pr.htm, 4 pages (last updated on Feb. 9, 2005).

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm, 2 pages.

Purdy, et al., "Arteriovenous malformations of the brain: choosing embolic materials to enhance safety and ease of excision", *J Neurosurg*, vol. 77, No. 2, pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (English Abstract included).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (English Summary included).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rubin, "Molecular Biology of the Tumor Stroma—A Target for Novel Therapy," Uppsala Universitet, http://www.imbim.uu.se/forskning/rubinresearch.html, 5 pages (last updated on Nov. 18, 2005).

Rump, A. et al., "Pharmacokinetics of Intraarterial Mitomycin C in the Chemoembolisation Treatment of Liver Metastases," *Gen. Pharmac.*, 27(4):669-671 (1996).

Ruoslahti, "Drug targeting to specific vascular sites," *Drug Discov. Today*, 7(22):1138-1143 (Nov. 2002).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (English Abstract included).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Wickham, "Ligand-directed targeting of genes to the site of disease," *Nat. Med.*, 9(1):135-139 (Jan. 2003).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Wong et al., "In Vivo Vascular Engineering: Directed Migration of Smooth Muscle Cells to Limit Neointima," *Tissue Engineering*, 8(2):189-199 (2002).

Worthington-Kirsch RL, "Interventionalists offer management option for uterine fibroids," *Diagnostic Imaging*; 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Degradation behaviors of biodegradable macroporous scaffolds prepared by gas foaming of effervescent salts," *J. Biomed. Mater. Res.*, 55:401-408 (2001).

Yoon et al., "Immobilization of cell adhesive RGD peptide onto the surface of highly porous biodegradable polymer scaffolds fabricated by a gas foaming/salt leaching method," *Biomaterials*, 25:5613-5620 (2004).

Yoon et al., "Surface Immobilization of Galactose onto Aliphatic Biodegradable polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," Zhong Hua Fang-She Xue ZaZhi, 23(6):330-332 (1989).

Zou, Ying-hua, et al. "Experimental Canine Hapatic Artery Embolization with Polyvinyl Alcohol Microspheres," Translation, Zhong Hua Fang-She Xue ZaZhi, 23(6):330-332 (1989).

\* cited by examiner

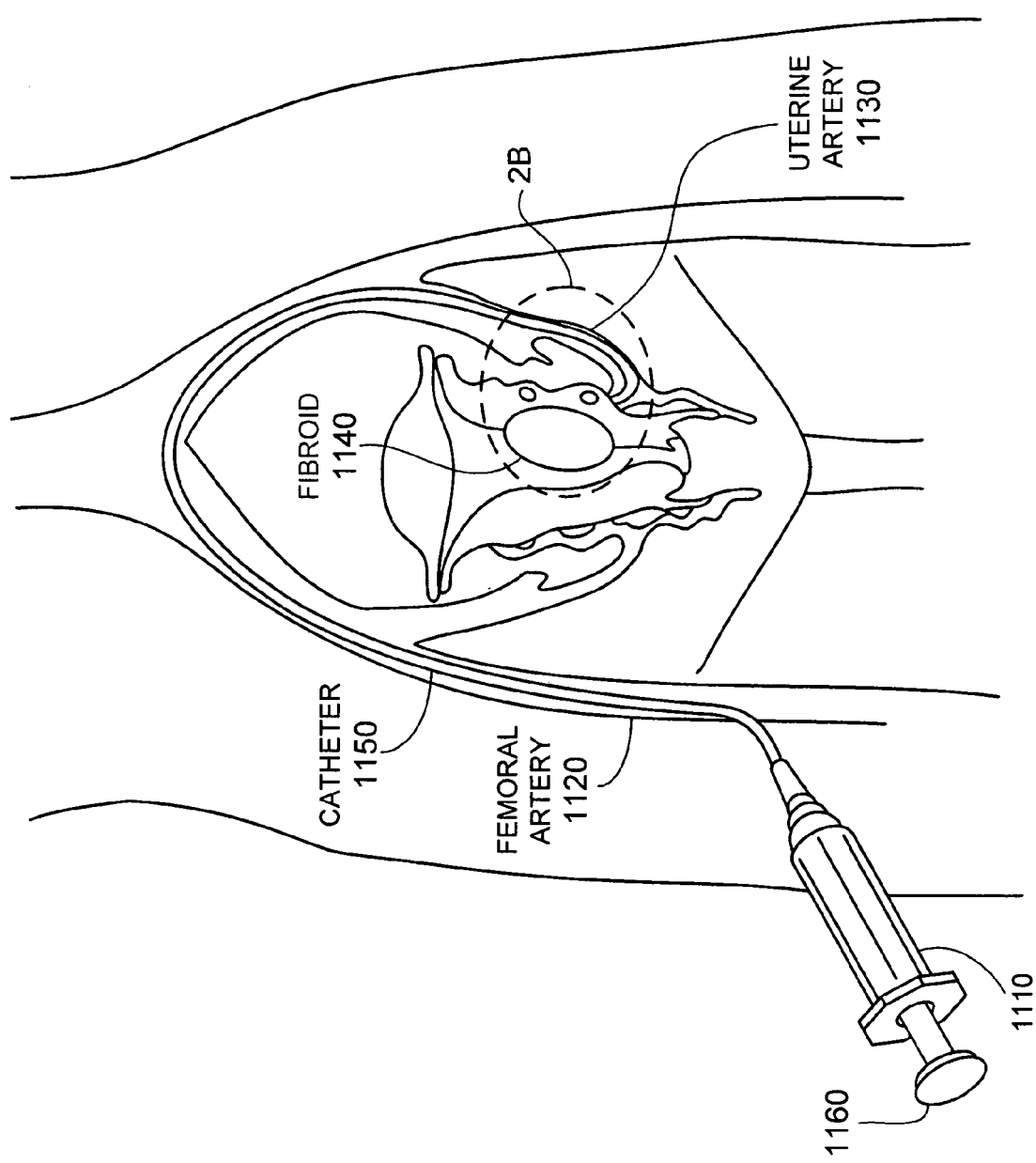

BLOCK COPOLYMER PARTICLES

TECHNICAL FIELD

The invention relates to block copolymer particles, and to related compositions and methods.

BACKGROUND

Agents, such as therapeutic agents, can be delivered systemically, for example, by injection through the vascular system or oral ingestion, or they can be applied directly to a site where treatment is desired. In some cases, particles are used to deliver a therapeutic agent to a target site. In the case of delivery of a therapeutic agent, it is often desirable that the therapeutic agent be delivered at desired dosages for an extended period of time.

SUMMARY

In one aspect, the invention features a particle that includes a biocompatible block copolymer with at least one block having a glass transition temperature of at most 37° C. and at least one block having a glass transition temperature of greater than 37° C. The particle has a diameter of less than about 100 microns, from about 300 microns to about 500 microns, from about 700 microns to about 900 microns, or from about 1,000 microns to about 1,200 microns.

In another aspect, the invention features a particle that includes a biocompatible block copolymer with at least one block having a glass transition temperature of at most 37° C. and at least one block having a glass transition temperature of greater than 37° C. The particle has a diameter of about 1,050 microns or more (e.g., about 1,060 microns or more, about 1,070 microns or more, about 1,080 microns or more, about 1,090 microns or more, about 1,100 microns or more).

In an additional aspect, the invention features a particle that includes a block copolymer with the formula $X\text{-}(AB)_n$, in which A is a block having a glass transition temperature of at most 37° C., B is a block having a glass transition temperature of greater than 37° C., n is a positive whole number, and X is an initiator. The particle has a diameter of less than about 100 microns, from about 300 microns to about 500 microns, from about 700 microns to about 900 microns, or from about 1,000 microns to about 1,200 microns.

In a further aspect, the invention features a particle that includes a block copolymer having the formula $X\text{-}(AB)_n$, in which A is a block having a glass transition temperature of at most 37° C., B is a block having a glass transition temperature of greater than 37° C., n is a positive whole number, and X is an initiator. The particle has a diameter of about 1,050 microns or more (e.g., about 1,060 microns or more, about 1,070 microns or more, about 1,080 microns or more, about 1,090 microns or more, about 1,100 microns or more).

In another aspect, the invention features a particle that has a matrix including a biocompatible block copolymer including at least one block having a glass transition temperature of at most 37° C. and at least one block having a glass transition temperature of greater than 37° C. The particle also includes at least one sub-particle (e.g., a plurality of sub-particles) that is at least partially disposed within the matrix. The particle has a diameter of about 3,000 microns or less (e.g., from about two microns to about 3,000 microns, less than about 100 microns, from about 300 microns to about 500 microns, from about 700 microns to about 900 microns, from about 1,000 microns to about 1,200 microns).

In a further aspect, the invention features a particle that includes a matrix including a biocompatible block copolymer having at least one block with a glass transition temperature of at most 37° C. and at least one block with a glass transition temperature of greater than 37° C. The particle also includes at least one sub-particle that is at least partially disposed within the matrix. The particle has a diameter of about 1,050 microns or more.

In an additional aspect, the invention features a particle that has a matrix including a biocompatible block copolymer having the formula $X\text{-}(AB)_n$, in which A is a block having a glass transition temperature of at most 37° C., B is a block having a glass transition temperature of greater than 37° C., n is a positive whole number, and X is an initiator. The particle also includes at least one sub-particle that is at least partially disposed within the matrix. The particle has a diameter of about 3,000 microns or less (e.g., from about two microns to about 3,000 microns, less than about 100 microns, from about 300 microns to about 500 microns, from about 700 microns to about 900 microns, from about 1,000 microns to about 1,200 microns).

In a further aspect, the invention features a particle that includes a matrix including a biocompatible block copolymer having the formula $X\text{-}(AB)_n$, and at least one sub-particle that is at least partially disposed within the matrix. The particle has a diameter of about 1,050 microns or more, and A is a block having a glass transition temperature of at most 37° C., B is a block having a glass transition temperature of greater than 37° C., n is a positive whole number, and X is an initiator.

In an additional aspect, the invention features a composition including a plurality of particles, at least some of the particles having a diameter of less than about 100 microns, from about 300 microns to about 500 microns, from about 700 microns to about 900 microns, or from about 1,000 microns to about 1,200 microns. At least some of the particles having a diameter of at less than about 100 microns, from about 300 microns to about 500 microns, from about 700 microns to about 900 microns, or from about 1,000 microns to about 1,200 microns include a biocompatible block copolymer including at least one block having a glass transition temperature of at most 37° C. and at least one block having a glass transition temperature of greater than 37° C. The composition also includes a carrier fluid, the plurality of particles being in the carrier fluid.

In a further aspect, the invention features a composition including a plurality of particles, at least some of the particles having a diameter of about 1,050 microns or more (e.g., about 1,060 microns or more, about 1,070 microns or more, about 1,080 microns or more, about 1,090 microns or more, about 1,100 microns or more). At least some of the particles having a diameter of about 1,050 microns or more include a biocompatible block copolymer including at least one block having a glass transition temperature of at most 37° C. and at least one block having a glass transition temperature of greater than 37° C. The composition also includes a carrier fluid, the plurality of particles being in the carrier fluid.

In another aspect, the invention features a composition including a plurality of particles, at least some of the plurality of particles having a diameter of less than about 100 microns, from about 300 microns to about 500 microns, from about 700 microns to about 900 microns, or from about 1,000 microns to about 1,200 microns. At least some of the particles having a diameter of less than about 100 microns, from about 300 microns to about 500 microns, from about 700 microns to about 900 microns, or from about 1,000 microns to about 1,200 microns include a block copolymer. The block copolymer has the formula $X\text{-}(AB)_n$, in which A is a block having a glass transition temperature of at most 37° C., B is a block having a glass transition temperature of greater than 37° C., n is a positive whole number, and X is an initiator. The composition also includes a carrier fluid, the plurality of particles being in the carrier fluid.

In an additional aspect, the invention features a composition including a plurality of particles, at least some of the plurality of particles having a diameter of about 1,050 microns or more (e.g., about 1,060 microns or more, about 1,070 microns or more, about 1,080 microns or more, about 1,090 microns or more, about 1,100 microns or more). At least some of the particles having a diameter of about 1,050 microns or more include a block copolymer. The block copolymer has the formula $X\text{-}(AB)_n$, in which A is a block having a glass transition temperature of at most 37° C., B is a block having a glass transition temperature of greater than 37° C., n is a positive whole number, and X is an initiator. The composition also includes a carrier fluid, the plurality of particles being in the carrier fluid.

In a further aspect, the invention features a method of making particles. The method includes contacting an aqueous first solution with a second solution while the aqueous first solution is being mixed (e.g., homogenized), to form a mixture. The second solution includes a solvent and a biocompatible block copolymer having at least one block with a glass transition temperature of at most 37° C. and at least one block with a glass transition temperature of greater than 37° C. At least some of the particles have a diameter of about 3,000 microns or less.

In another aspect, the invention features a method of making particles. The method includes contacting an aqueous first solution with a second solution while the aqueous first solution is being mixed (e.g., homogenized), to form a mixture. The second solution includes a solvent and a biocompatible block copolymer. The biocompatible block copolymer has the formula $X\text{-}(AB)_n$, in which A is a block having a glass transition temperature of at most 37° C., B is a block having a glass transition temperature of greater than 37° C., n is a positive whole number, and X is an initiator. At least some of the particles have a diameter of about 3,000 microns or less.

In an additional aspect, the invention features a method of making particles. The method includes contacting an aqueous first solution with a second solution including a solvent and a biocompatible block copolymer to form a mixture. The biocompatible block copolymer has at least one block with a glass transition temperature of at most 37° C. and at least one block with a glass transition temperature of greater than 37° C. The method also includes mixing (e.g., homogenizing) the mixture. At least some of the particles have a diameter of about 3,000 microns or less.

In another aspect, the invention features a method of making particles. The method includes contacting an aqueous first solution with a second solution including a solvent and a biocompatible block copolymer, to form a mixture. The method also includes mixing (e.g., homogenizing) the mixture. The biocompatible block copolymer has the formula $X\text{-}(AB)_n$, in which A is a block having a glass transition temperature of at most 37° C., B is a block having a glass transition temperature of greater than 37° C., n is a positive whole number, and X is an initiator. At least some of the particles have a diameter of about 3,000 microns or less.

In an additional aspect, the invention features a method of making particles. The method includes contacting an aqueous first solution with a second solution including a solvent and a biocompatible block copolymer, to form a mixture. The biocompatible block copolymer has at least one block with a glass transition temperature of at most 37° C. and at least one block with a glass transition temperature of greater than 37° C. At least some of the particles include a first therapeutic agent that is dispersed throughout the particles, and at least some of the particles have a diameter of about 3,000 microns or less.

In a further aspect, the invention features a method of making particles. The method includes contacting an aqueous first solution with a second solution including a solvent and a biocompatible block copolymer, to form a mixture. The biocompatible block copolymer has the formula $X\text{-}(AB)_n$, in which A is a block having a glass transition temperature of at most 37° C., B is a block having a glass transition temperature of greater than 37° C., n is a positive whole number, and X is an initiator. At least some of the particles include a first therapeutic agent that is dispersed throughout the particles, and at least some of the particles have a diameter of about 3,000 microns or less.

In an additional aspect, the invention features a method including administering to a patient a therapeutically effective amount of a composition including particles. At least some of the particles have a diameter of less than about 100 microns, from about 300 microns to about 500 microns, from about 700 microns to about 900 microns, or from about 1,000 microns to about 1,200 microns. At least some of the particles having a diameter of less than about 100 microns, from about 300 microns to about 500 microns, from about 700 microns to about 900 microns, or from about 1,000 microns to about 1,200 microns include a block copolymer having at least one block with a glass transition temperature of at most 37° C. and at least one block with a glass transition temperature of greater than 37° C.

In another aspect, the invention features a method including administering to a patient a therapeutically effective amount of a composition including particles. At least some of the particles have a diameter of about 1,050 microns or more (e.g., about 1,060 microns or more, about 1,070 microns or more, about 1,080 microns or more, about 1,090 microns or more, about 1,100 microns or more). At least some of the particles having a diameter of about 1,050 microns or more include a block copolymer having at least one block with a glass transition temperature of at most 37° C. and at least one block with a glass transition temperature of greater than 37° C.

In a further aspect, the invention features a method including administering to a patient a therapeutically effective amount of a composition including particles. At least some of the particles have a diameter of less than about 100 microns, from about 300 microns to about 500 microns, from about 700 microns to about 900 microns, or from about 1,000 microns to about 1,200 microns. At least some of the particles having a diameter of less than about 100 microns, from about 300 microns to about 500 microns, from about 700 microns to about 900 microns, or from about 1,000 microns to about 1,200 microns include a block copolymer having the formula $X\text{-}(AB)_n$, in which A is a block having a glass transition temperature of at most 37° C., B is a block having a glass transition temperature of greater than 37° C., n is a positive whole number, and X is an initiator.

In a further aspect, the invention features a method including administering to a patient a therapeutically effective amount of a composition including particles. At least some of the particles have a diameter of about 1,050 microns or more (e.g., about 1,060 microns or more, about 1,070 microns or more, about 1,080 microns or more, about 1,090 microns or more, about 1,100 microns or more). At least some of the particles having a diameter of about 1,050 microns or more include a block copolymer having the formula $X\text{-}(AB)_n$, in which A is a block having a glass transition temperature of at most 37° C., B is a block having a glass transition temperature of greater than 37° C., n is a positive whole number, and X is an initiator.

Embodiments can also include one or more of the following.

In some embodiments, the block copolymer can be biocompatible.

In certain embodiments, a block having a glass transition temperature of at most 37° C. can be a polyolefin block. In some embodiments, a block having a glass transition temperature of at most 37° C. can include at least one isobutylene monomer.

In certain embodiments, a block having a glass transition temperature of greater than 37° C. can be a vinyl aromatic block or a methacrylate block. In some embodiments, a block having a glass transition temperature of greater than 37° C. can include at least one monomer selected from styrene, α-methylstyrene, and combinations thereof.

In certain embodiments, the block copolymer can have the formula $X-(AB)_n$, in which n is a positive number and X is an initiator. In some embodiments, A can be a block having a glass transition temperature of at most 37° C., and/or can be a polyolefin block. In certain embodiments, B can be a block having a glass transition temperature of greater than 37° C., and/or can be a vinyl aromatic block or a methacrylate block.

In some embodiments, the block copolymer can have the formula BAB or ABA, in which A is a block having a glass transition temperature of at most 37° C., and B is a block having a glass transition temperature of greater than 37° C. In certain embodiments, the block copolymer can have the formula has the formula $B(AB)_n$ or $A(BA)_n$, in which A is a block having a glass transition temperature of at most 37° C., B is a block having a glass transition temperature of greater than 37° C., and n is a positive whole number.

In certain embodiments, A can be a polyolefin block (e.g., a polyolefin block that includes at least one isobutylene monomer). In some embodiments, B can be a vinyl aromatic block or a methacrylate block. In certain embodiments, B can include at least one monomer selected from methylmethacrylate, ethylmethacrylate, hydroxyethyl methacrylate, and combinations thereof. In some embodiments, the polyolefin block can include at least one isobutylene monomer and/or the vinyl aromatic block can include at least one monomer selected from styrene, α-methylstyrene, and combinations thereof. In certain embodiments, A can have the formula $-(CRR'-CH_2)_n-$, in which R and R' are linear or branched aliphatic groups or cyclic aliphatic groups, and B can be a methacrylate block or a vinyl aromatic block.

In some embodiments, the block copolymer can include from about 45 mol percent to about 95 mol percent of polyolefin blocks.

In certain embodiments, the block copolymer can have a molecular weight of more than about 40,000 Daltons (e.g., from about 80,000 Daltons to about 300,000 Daltons). In some embodiments, the block copolymer can include polyolefin blocks having a molecular weight (e.g., a combined molecular weight) of from about 60,000 Daltons to about 200,000 Daltons and vinyl aromatic blocks having a molecular weight (e.g., a combined molecular weight) of from about 20,000 Daltons to about 100,000 Daltons.

In certain embodiments, the particle can have a diameter of less than about 100 microns. In some embodiments, the particle can have a diameter of from about 300 microns to about 500 microns, from about 700 microns to about 900 microns, or from about 1,000 microns to about 1,200 microns. In certain embodiments, the particle can have a diameter of about 1,050 microns or more (e.g., 1,060 microns or more, 1,070 microns or more, 1,080 microns or more, 1,090 microns or more, 1,100 microns or more, 1,150 microns or more). In some embodiments, the particle can have a diameter of about 3,000 microns or less (e.g., from about two microns to about 3,000 microns).

In some embodiments, the particle (e.g., the block copolymer) can include a therapeutic agent (e.g., from about 0.1 weight percent to about 70 weight percent of a therapeutic agent). In certain embodiments, the therapeutic agent can be dispersed throughout the particle. In some embodiments, the particle can include at least two therapeutic agents that are different from each other.

In certain embodiments, the particle can further include at least one other polymer (e.g., in a blend with the block copolymer). The other polymer can also be a copolymer (e.g., a block copolymer), or can be a homopolymer. In some embodiments, the other polymer can be a polyvinyl alcohol, a polyacrylic acid, a polymethacrylic acid, a poly vinyl sulfonate, a carboxymethyl cellulose, a hydroxyethyl cellulose, a substituted cellulose, a polyacrylamide, a polyethylene glycol, a polyamide, a polyurea, a polyurethane, a polyester, a polyether, a polystyrene, a polysaccharide, a polylactic acid, a polyethylene, a polymethylmethacrylate, a polycaprolactone, a polyglycolic acid, a poly(lactic-co-glycolic) acid, or a styrene maleic anhydride copolymer. In certain embodiments, combinations of two or more of these polymers can be used.

In some embodiments, the particle can further include a bioabsorbable material. In certain embodiments, the particle can further include a hydrogel (e.g., polyacrylamide co-acrylic acid). The hydrogel may be cross-linked or may not be cross-linked. In some such embodiments, the block copolymer can form a coating over the hydrogel, and/or the hydrogel can form a coating over the block copolymer.

In some embodiments, the block copolymer can form a coating on the particle.

In certain embodiments, the carrier fluid can include a saline solution and/or a contrast agent.

In some embodiments, the method can include forming a suspension from the mixture and contacting the suspension with an aqueous third solution.

In certain embodiments, the aqueous first solution can be mixed at a speed of at most about 10,000 revolutions per minute (e.g., at most about 5,000 revolutions per minute, at most about 1,500 revolutions per minute). In some embodiments, the method can include mixing the mixture at a speed of at most about 10,000 revolutions per minute (e.g., at most about 6,000 revolutions per minute), and/or at least about 1,000 revolutions per minute. In certain embodiments, the method can include mixing the mixture at a temperature of at least about 30° C. (e.g., at least about 35° C.).

In some embodiments, the aqueous first solution and/or the second solution can include a therapeutic agent.

In certain embodiments, the method of administration can be by percutaneous injection. In some embodiments, the composition can be used to treat a cancer condition (e.g., ovarian cancer, colorectal cancer, thyroid cancer, gastrointestinal cancer, breast cancer, prostate cancer, lung cancer). The method can include embolizing a lumen of a subject (e.g., a lumen that is associated with a cancer condition).

Embodiments can include one or more of the following advantages.

The particles can be relatively durable and/or flexible, and thus can be unlikely to be damaged during storage, delivery, or use. In some embodiments (e.g., embodiments in which the particles are formed of styrene-isobutylene-styrene), the particles can have a relatively high mechanical integrity (e.g., such that contact with the walls of a catheter will not harm the particles). In certain embodiments (e.g., embodiments in which the particles are formed of styrene-isobutylene-styrene), the particles can be relatively flexible, and thus can be adapted for use in many different environments. In some embodiments in which the particles are relatively flexible, the particles can include a swellable material (e.g., a hydrogel), such that the particles can be delivered to a target site while the particles are in a relatively compressed state, and can later expand at the target site as a result of swelling of the swellable material (e.g., to enhance occlusion). In such embodiments, the particles can have good deliverability, while also being effective in occluding the target site.

The particles can be used to deliver one or more therapeutic agents to a target site effectively and efficiently, and/or to occlude the target site. In some embodiments, the particles can be used to deliver a metered dose of a therapeutic agent to a target site over a period of time. In certain embodiments, the release of a therapeutic agent from the particles can be delayed until the particles have reached a target site. For example, the particles can include a bioerodible coating that erodes during delivery, such that when the particles reach the target site, they can begin to release the therapeutic agent.

The particles can be used to deliver multiple therapeutic agents, either to the same target site, or to different target sites. For example, the particles can deliver one type of therapeutic agent (e.g., an anti-inflammatory) as the particles are being delivered to a target site, and another type of therapeutic agent (e.g., a chemotherapeutic agent) once the particles have reached the target site.

Features and advantages are in the description, drawings, and claims.

DESCRIPTION OF DRAWINGS

FIG. 2A is a schematic illustrating an embodiment of injection of a composition including particles into a vessel.

DETAILED DESCRIPTION

Figure 1:
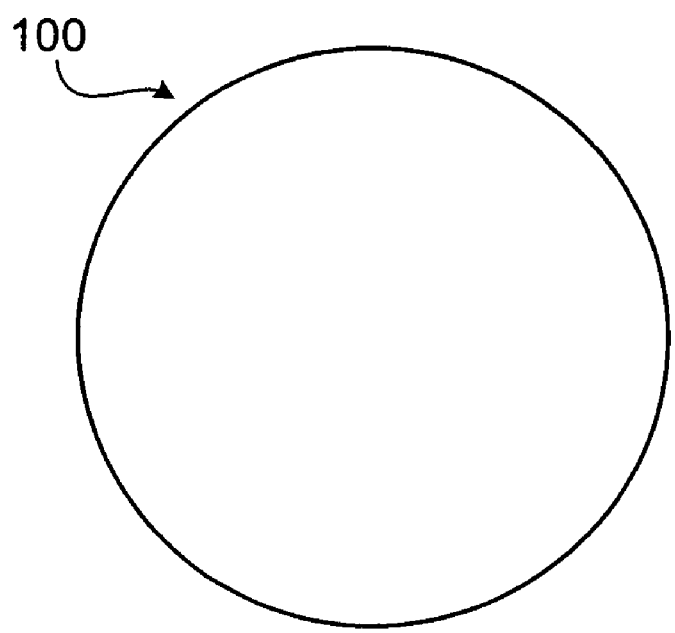
FIG. 1 is a side view of an embodiment of a particle.

FIG. 1 shows a particle 100 that can be used to deliver one or more therapeutic agents (e.g., drugs) to a target site within the body. The therapeutic agents can be included on particle 100 and/or within particle 100 (e.g., dispersed throughout particle 100). Particle 100 is formed of a block copolymer that includes a first block having a glass transition temperature ($T_g$) of at most 37° C. and a second block having a glass transition temperature of greater than 37° C.

Block copolymers are copolymers that contain two or more differing polymer blocks selected, for example, from homopolymer blocks, copolymer blocks (e.g., random copolymer blocks, statistical copolymer blocks, gradient copolymer blocks, periodic copolymer blocks), and combinations of homopolymer and copolymer blocks. A polymer "block" refers to a grouping of multiple copies of a single type (homopolymer block) or multiple types (copolymer block) of constitutional units. A "chain" is an unbranched polymer block. In some embodiments, a polymer block can be a grouping of at least two (e.g., at least five, at least 10, at least 20, at least 50, at least 100, at least 250, at least 500, at least 750) and/or at most 1000 (e.g., at most 750, at most 500, at most 250, at most 100, at most 50, at most 20, at most 10, at most five) copies of a single type or multiple types of constitutional units. A polymer block may take on any of a number of different architectures.

In some embodiments, the block copolymer in particle 100 can include a central block having a glass transition temperature of at most 37° C. and end blocks each having a glass transition temperature of greater than 37° C. In certain embodiments, the block copolymer can have one of the following general structures:

(a) BAB or ABA (linear triblock),
(b) B(AB)$_n$ or A(BA)$_n$ (linear alternating block), or
(c) X-(AB)$_n$ or X-(BA)$_n$ (includes diblock, triblock and other radial block copolymers), where A is a block having a glass transition temperature of at most 37° C., B is a block having a glass transition temperature of greater than 37° C., n is a positive whole number and X is an initiator (e.g., a monofunctional initiator, a multifunctional initiator).

The X-(AB)$_n$ structures are frequently referred to as diblock copolymers (when n=1) or triblock copolymers (when n=2). (This terminology disregards the presence of the initiator, for example, treating A-X-A as a single A block with the triblock therefore denoted as BAB.) Where n=3 or more, these structures are commonly referred to as star-shaped block copolymers.

As described above, the A blocks have a glass transition temperature of at most 37° C. In some embodiments, the A blocks can have a glass transition temperature of at most about 30° C. (e.g., at most about 25° C., at most about 20° C., at most about 10° C., at most about 0° C., at most about −10° C., at most about −20° C., at most about −30° C., at most about −50° C., at most about −70° C., at most about −90° C.). As referred to herein, the glass transition temperature of a material (e.g., a polymer block) is determined according to ASTM E1356. Examples of blocks having a glass transition temperature of at most 37° C. when the blocks are in the dry state (e.g., in powder form) include blocks including at least one of the following monomers:

(1) acrylic monomers including:
  (a) alkyl acrylates, such as methyl acrylate, ethyl acrylate, propyl acrylate, isopropyl acrylate (e.g., isotactic isopropyl acrylate), butyl acrylate, sec-butyl acrylate, isobutyl acrylate, cyclohexyl acrylate, 2-ethylhexyl acrylate, dodecyl acrylate and hexadecyl acrylate,
  (b) arylalkyl acrylates, such as benzyl acrylate,
  (c) alkoxyalkyl acrylates, such as 2-ethoxyethyl acrylate and 2-methoxyethyl acrylate,
  (d) halo-alkyl acrylates, such as 2,2,2-trifluoroethyl acrylate, and
  (e) cyano-alkyl acrylates, such as 2-cyanoethyl acrylate;
(2) methacrylic monomers including:
  (a) alkyl methacrylates, such as butyl methacrylate, hexyl methacrylate, 2-ethylhexyl methacrylate, octyl methacrylate, dodecyl methacrylate, hexadecyl methacrylate and octadecyl methacrylate, and
  (b) aminoalkyl methacrylates, such as diethylaminoethyl methacrylate and 2-tert-butyl-aminoethyl methacrylate;
(3) vinyl ether monomers including:
  (a) alkyl vinyl ethers, such as methyl vinyl ether, ethyl vinyl ether, propyl vinyl ether, butyl vinyl ether, isobutyl vinyl ether, 2-ethylhexyl vinyl ether and dodecyl vinyl ether;
(4) cyclic ether monomers, such as tetrahydrofuran, trimethylene oxide, ethylene oxide, propylene oxide, methyl glycidyl ether, butyl glycidyl ether, allyl glycidyl ether, epibromohydrin, epichlorohydrin, 1,2-epoxybutane, 1,2-epoxyoctane, and 1,2-epoxydecane;
(5) ester monomers (other than acrylates and methacrylates), such as ethylene malonate, vinyl acetate, and vinyl propionate;
(6) alkene monomers, such as ethylene, propylene, isobutylene, 1-butene, trans-butadiene, 4-methyl pentene, 1-octene and other α-olefins, cis-isoprene, and trans-isoprene;
(7) halogenated alkene monomers, such as vinylidene chloride, vinylidene fluoride, cis-chlorobutadiene, and trans-chlorobutadiene;
(8) siloxane monomers, such as dimethylsiloxane, diethylsiloxane, methylethylsiloxane, methylphenylsiloxane, and diphenylsiloxane; and
(9) maleic monomers, such as maleic anhydride.

In certain embodiments, the A blocks can include one or more derivatives of the above monomers.

In some embodiments, the A blocks can be based upon one or more polyolefins. In certain embodiments, the A blocks can be polyolefinic blocks having alternating quaternary and secondary carbons of the general formulation: —(CRR'—CH$_2$)$_n$—, where R and R' are linear or branched aliphatic groups (e.g., methyl, ethyl, propyl, isopropyl, butyl, isobutyl) or cyclic aliphatic groups (e.g., cyclohexane, cyclopentane), with and without pendant groups. For example, the A blocks can be polyolefinic blocks having the above formula, in which R and R' are the same. As an example, the A blocks can be based on isobutylene:

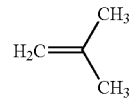

(i.e., in which R and R' are both methyl groups).

In some embodiments, the block copolymer can include at least about 40 mol percent (e.g., from about 45 mol percent to about 95 mol percent) of polyolefin blocks.

As described above, the B blocks have a glass transition temperature of greater than 37° C. In some embodiments, the B blocks can have a glass transition temperature of at least about 40° C. (e.g., at least about 50° C., at least about 70° C., at least about 90° C., at least about 100° C., at least about 120° C.). Examples of blocks having a glass transition temperature of greater than 37° C. when the blocks are in the dry state (e.g., in powder form) include blocks including at least one of the following monomers:

(1) vinyl aromatic monomers including:
  (a) unsubstituted vinyl aromatics, such as atactic styrene, isotactic styrene and 2-vinyl naphthalene,
  (b) vinyl-substituted aromatics, such as α-methyl styrene, and
  (c) ring-substituted vinyl aromatics including ring-alkylated vinyl aromatics (e.g., 3-methylstyrene, 4-methylstyrene, 2,4-dimethylstyrene, 2,5-dimethylstyrene, 3,5-dimethylstyrene, 2,4,6-trimethylstyrene, 4-tert-butylstyrene), ring-alkoxylated vinyl aromatics (e.g., 4-methoxystyrene, 4-ethoxystyrene), ring-halogenated vinyl aromatics (e.g., 2-chlorostyrene, 3-chlorostyrene, 4-chlorostyrene, 2,6-dichlorostyrene, 4-bromostyrene, 4-fluorostyrene), ring-ester-substituted vinyl aromatics (e.g., 4-acetoxystyrene), and hydroxyl styrene;
(2) other vinyl monomers including:
  (a) vinyl esters such as vinyl benzoate, vinyl 4-tert-butyl benzoate, vinyl cyclohexanoate, vinyl pivalate, vinyl trifluoroacetate, vinyl butyral,
  (b) vinyl amines such as 2-vinyl pyridine, 4-vinyl pyridine, and vinyl carbazole,
  (c) vinyl halides such as vinyl chloride and vinyl fluoride, (d) alkyl vinyl ethers such as tert-butyl vinyl ether and cyclohexyl vinyl ether, and
(e) other vinyl compounds such as vinyl ferrocene;
(3) other aromatic monomers including acenaphthalene and indene;
(4) methacrylic monomers including:
   (a) methacrylic acid anhydride,
   (b) methacrylic acid esters (methacrylates) including
      (i) alkyl methacrylates such as atactic methyl methacrylate, syndiotactic methyl methacrylate, ethyl methacrylate, isopropyl methacrylate, isobutyl methacrylate, t-butyl methacrylate and cyclohexyl methacrylate,
      (ii) aromatic methacrylates such as phenyl methacrylate and including aromatic alkyl methacrylates such as benzyl methacrylate,
      (iii) hydroxyalkyl methacrylates such as 2-hydroxyethyl methacrylate and 2-hydroxypropyl methacrylate,
      (iv) additional methacrylates including isobornyl methacrylate and trimethylsilyl methacrylate, and
   (c) other methacrylic-acid derivatives including methacrylonitrile;
(5) acrylic monomers including:
   (a) certain acrylic acid esters such as tert-butyl acrylate, hexyl acrylate and isobornyl acrylate,
   (b) other acrylic-acid derivatives including acrylonitrile; and
(6) silicate monomers including polyhedral oligomeric silsesquioxane (POSS) monomers.

In certain embodiments, the B blocks can include one or more derivatives of the above monomers.

In certain embodiments, the B blocks can be polymers of methacrylates or polymers of vinyl aromatics. In some embodiments, the B blocks can be either: (a) made from monomers of styrene:

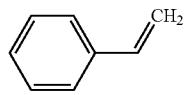

or styrene derivatives (e.g., α-methylstyrene, ring-alkylated styrenes or ring-halogenated styrenes) or mixtures thereof, or (b) made from monomers of methylmethacrylate, ethylmethacrylate, hydroxyethyl methacrylate, or mixtures thereof.

In some embodiments, the block copolymer can include at least about five mol percent (e.g., at least about 30 mol percent, about 60 mol percent) of styrene blocks.

An example of one of the above copolymers is styrene-isobutylene-styrene ("SIBS"), in which the A blocks are based on isobutylene, and the B blocks are based on styrene. Another example of one of the above copolymers is styrene maleic anhydride ("SMA"), in which the A blocks are based on maleic anhydride and the B blocks are based on styrene.

Typically, the combined molecular weight of the block copolymer can be more than about 40,000 Daltons (e.g., more than about 60,000 Daltons). For example, the combined molecular weight of the block copolymer can be from about 80,000 Daltons to about 300,000 Daltons (e.g., from about 90,000 Daltons to about 300,000 Daltons). In some embodiments (e.g., embodiments in which the A blocks are polyolefin blocks), the combined molecular weight of the A blocks can be from about 60,000 Daltons to about 200,000 Daltons.

In certain embodiments (e.g., embodiments in which the B blocks are vinyl aromatic blocks), the combined molecular weight of the B blocks can be from about 20,000 Daltons to about 100,000 Daltons.

Generally, the properties of the block copolymer used in particle 100 can depend upon the lengths of the A block chains and B block chains in the block copolymer, and/or on the relative amounts of A block and B blocks in the block copolymer.

As an example, in some embodiments, blocks with a glass transition temperature of at most 37° C. may be elastomeric. In such embodiments, the elastomeric properties of the block copolymer can depend on the length of the A block chains. In certain embodiments, the A block chains can have a weight average molecular weight of from about 2,000 Daltons to about 30,000 Daltons. In such embodiments, the block copolymer (and, therefore, particle 100) may be relatively inelastic. In some embodiments, the A block chains can have a weight average molecular weight of at least about 40,000 Daltons. In such embodiments, the block copolymer (and, therefore, particle 100) may be relatively soft and/or rubbery.

As another example, in certain embodiments, blocks with a glass transition temperature of greater than 37° C. may be relatively hard at 37° C. In such embodiments, the hardness of the block copolymer at 37° C. can depend on the relative amount of B blocks in the block copolymer. In some embodiments, the block copolymer can have a hardness of from about Shore 20A to about Shore 75D (e.g., from about Shore 40A to about Shore 90A). In certain embodiments, a copolymer with a desired degree of hardness may be formed by varying the proportions of the A and B blocks in the copolymer, with a lower relative proportion of B blocks resulting in a copolymer of lower hardness, and a higher relative proportion of B blocks resulting in a copolymer of higher hardness. As a specific example, high molecular weight (i.e., greater than 100,000 Daltons) polyisobutylene is a relatively soft and gummy material with a Shore hardness of approximately 10A. By comparison, polystyrene is much harder, typically having a Shore hardness on the order of 100D. As a result, when blocks of polyisobutylene and styrene are combined, the resulting copolymer can have a range of hardnesses from as soft as Shore 10A to as hard as Shore 100D, depending upon the relative amounts of polystyrene and polyisobutylene in the copolymer. In some embodiments, from about two mol percent to about 25 mol percent (e.g., from about five mol percent to about 20 mol percent) of polystyrene can be used to form a block copolymer with a hardness of from about Shore 30A to about Shore 90A (e.g., from about Shore 35A to about Shore 70A).

Polydispersity (the ratio of weight average molecular weight to number average molecular weight) gives an indication of the molecular weight distribution of the copolymer, with values significantly greater than four indicating a broad molecular weight distribution. When all molecules within a sample are the same size, the polydispersity has a value of one. Typically, copolymers used in particle 100 can have a relatively tight molecular weight distribution, with a polydispersity of from about 1.1 to about 1.7.

In some embodiments, one or more of the above-described copolymers can have a relatively high tensile strength. For example, triblock copolymers of polystyrene-polyisobutylene-polystyrene can have a tensile strength of at least about 2,000 psi (e.g., from about 2,000 psi to about 4,000 psi).

In certain embodiments, one or more of the above-described copolymers can be relatively resistant to cracking and/or other forms of degradation under in vivo conditions. Additionally or alternatively, one or more of the above-described polymers can exhibit excellent biocompatibility, including vascular compatibility. For example, the polymers can provoke minimal adverse tissue reactions, resulting in reduced polymorphonuclear leukocyte and reduced macrophage activity. In some embodiments, one or more of the above-described polymers can generally be hemocompatible, and can thereby minimize thrombotic occlusion of, for example, small vessels.

The above-described block copolymers can be made using any appropriate method known in the art. In some embodiments, the block copolymers can be made by a carbocationic polymerization process that includes an initial polymerization of a monomer or mixtures of monomers to form the A blocks, followed by the subsequent addition of a monomer or a mixture of monomers capable of forming the B blocks. Such polymerization reactions are described, for example, in Kennedy et al., U.S. Pat. No. 4,276,394; Kennedy, U.S. Pat. No. 4,316,973; Kennedy, 4,342,849; Kennedy et al., U.S. Pat. No. 4,910,321; Kennedy et al., U.S. Pat. No. 4,929,683; Kennedy et al., U.S. Pat. No. 4,946,899; Kennedy et al., U.S. Pat. No. 5,066,730; Kennedy et al., U.S. Pat. No. 5,122,572; and Kennedy et al., U.S. Pat. No. Re. 34,640. Each of these patents is incorporated herein by reference.

The techniques disclosed in these patents generally involve an "initiator", which can be used to create X-(AB)$_n$ structures, where X is the initiator, and n can be 1, 2, 3 or more. The initiator can be monofunctional or multifunctional. As noted above, the resulting molecules are referred to as diblock copolymers where n is 1, triblock copolymers (disregarding the presence of the initiator) where n is 2, and star-shaped block copolymers where n is 3 or more.

In general, the polymerization reaction can be conducted under conditions that minimize or avoid chain transfer and termination of the growing polymer chains. Steps can be taken to keep active hydrogen atoms (water, alcohol and the like) to a minimum. The temperature for the polymerization is usually from about −10° C. to about −90° C. (e.g., from about −60° C. to about −80° C.), although lower temperatures can be used.

Typically, one or more A blocks (e.g., polyisobutylene blocks) can be formed in a first step, followed by the addition of B blocks (e.g., polystyrene blocks) at the ends of the A blocks. More particularly, the first polymerization step is generally carried out in an appropriate solvent system, such as a mixture of polar and non-polar solvents (e.g., methyl chloride and hexanes). The reaction bath can contain the aforementioned solvent system, olefin monomer (e.g., isobutylene), an initiator (e.g., a tert-ester, tert-ether, tert-hydroxyl or tert-halogen containing compound, a cumyl ester of a hydrocarbon acid, an alkyl cumyl ether, a cumyl halide, a cumyl hydroxyl compound, or a hindered version of the above), and a coinitiator (e.g., a Lewis acid, such as boron trichloride or titanium tetrachloride). In some embodiments, electron pair donors (e.g., dimethyl acetamide, dimethyl sulfoxide, dimethyl phthalate) can be added to the solvent system. Additionally, proton-scavengers that scavenge water, such as 2,6-di-tert-butylpyridine, 4-methyl-2,6-di-tert-butylpyridine, 1,8-bis(dimethylamino)-naphthalene, or diisopropylethyl amine can be added.

The reaction is commenced by removing the tert-ester, tert-ether, tert-hydroxyl or tert-halogen (herein called the "tert-leaving groups") from the initiator by reacting the initiator with the Lewis acid. In place of the tert-leaving groups is a quasi-stable or "living" cation which is stabilized by the surrounding tertiary carbons, as well as the polar solvent system and electron pair donors. After obtaining the cation, the A block monomer (e.g., isobutylene) is introduced, and cationically propagates or polymerizes from each cation on the initiator. When the A block is polymerized, the propagated cations remain on the ends of the A blocks. The B block monomer (e.g., styrene) is then introduced, and polymerizes and propagates from the ends of the A block. Once the B blocks are polymerized, the reaction is terminated by adding a termination molecule such as methanol, water and the like.

Product molecular weights are generally determined by reaction time, reaction temperature, the nature and concentration of the reactants, and so forth. Consequently, different reaction conditions may produce different products. In general, synthesis of the desired reaction product is achieved by an iterative process in which the course of the reaction is monitored by the examination of samples taken periodically during the reaction—a technique widely employed in the art. To achieve the desired product, an additional reaction may be required in which reaction time and temperature, reactant concentration, and so forth are changed.

Additional details regarding cationic processes for making copolymers are found, for example, in Kennedy et al., U.S. Pat. No. 4,276,394; Kennedy, U.S. Pat. No. 4,316,973; Kennedy, 4,342,849; Kennedy et al., U.S. Pat. No. 4,910,321; Kennedy et al., U.S. Pat. No. 4,929,683; Kennedy et al., U.S. Pat. No. 4,946,899; Kennedy et al., U.S. Pat. No. 5,066,730; Kennedy et al., U.S. Pat. No. 5,122,572; and Kennedy et al., U.S. Pat. No. Re. 34,640, incorporated supra.

The block copolymer may be recovered from the reaction mixture by any of the usual techniques including evaporation of solvent, precipitation with a non-solvent such as an alcohol or alcohol/acetone mixture, followed by drying, and so forth. In addition, purification of the copolymer can be performed by sequential extraction in aqueous media, both with and without the presence of various alcohols, ethers and ketones.

In some embodiments, particle 100 can be formed of a block copolymer that includes one or more functional groups. The functional groups can be negatively charged or positively charged, and/or can be ionically bonded to the polymer. In some embodiments, the functional groups can enhance the biocompatibility of the polymer. Alternatively or additionally, the functional groups can enhance the clot-forming capabilities of the polymer. Examples of functional groups include phosphate groups, carboxylate groups, sulfonate groups, sulfate groups, phosphonate groups, and phenolate groups. For example, a polymer can be a sulfonated styrenic polymer, such as sulfonated SIBS. Sulfonation of styrene block copolymers is disclosed, for example, in Ehrenberg, et al., U.S. Pat. No. 5,468,574; Vachon et al., U.S. Pat. No. 6,306,419; and Berlowitz-Tarrant, et al., U.S. Pat. No. 5,840,387, all of which are incorporated herein by reference. Examples of other functionalized polymers include phosphated SIBS and carboxylated SIBS. In certain embodiments, a polymer can include more than one different type of functional group. For example, a polymer can include both a sulfonate group and a phosphate group. In some embodiments, a polymer that includes a functional group can be reacted with a cross-linking and/or gelling agent during particle formation. For example, a particle that includes a sulfonates group, such as sulfonated SIBS, may be reacted with a cross-linking and/or gelling agent such as calcium chloride. Functionalized polymers and cross-linking and/or gelling agents are described, for example, in Richard et al., U.S. patent application Ser. No. 10/927,868, filed on Aug. 27, 2004, and entitled "Embolization", which is incorporated herein by reference.

As described above, particle 100 can be used to deliver one or more therapeutic agents to a target site. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; proteins; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation, such as rapamycin); calcium entry blockers (e.g., verapamil, diltiazem, nifedipine); and survival genes which protect against cell death (e.g., anti-apoptotic Bcl-2 family factors and Akt kinase).

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in Kunz et al., U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

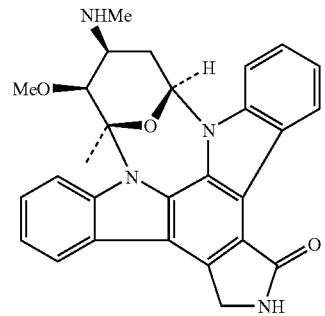

as well as diindoloalkaloids having one of the following general structures:

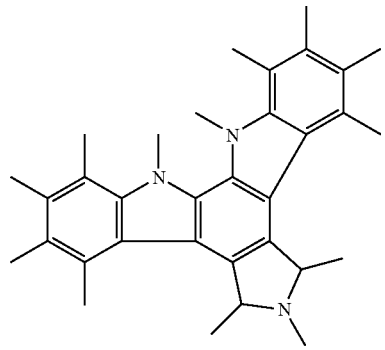

-continued

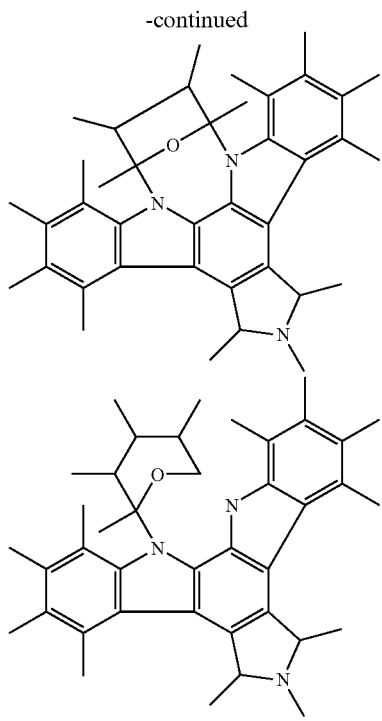

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclins and prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, anti-sense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, interleukins, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in DiMatteo et al., U.S. Patent Application Publication No. US 2004/0076582 A1, published on Apr. 22, 2004, and entitled "Agent Delivery Particle", and in Schwarz et al., U.S. Pat. No. 6,368,658, both of which are incorporated herein by reference.

In certain embodiments, in addition to or as an alternative to including therapeutic agents, particle 100 can include one or more radiopaque materials, materials that are visible by magnetic resonance imaging (MRI-visible materials), ferromagnetic materials, and/or contrast agents (e.g., ultrasound contrast agents). Radiopaque materials, MRI-visible materials, ferromagnetic materials, and contrast agents are described, for example, in Rioux et al., U.S. Patent Application Publication No. US 2004/0101564 A1, published on May 27, 2004, which is incorporated herein by reference.

In general, particle 100 can have a diameter of about 3,000 microns or less (e.g., from about two microns to about 3,000 microns, from about 10 microns to about 3,000 microns, from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns, from about 1,000 microns to about 1,200 microns). In some embodiments, particle 100 can have a diameter of about 3,000 microns or less (e.g., about 2,500 microns or less; about 2,000 microns or less; about 1,500 microns or less; about 1,200 microns or less; about 1,150 microns or less; about 1,100 microns or less; about 1,090 microns or less; about 1,080 microns or less; about 1,070 microns or less; about 1,060 microns or less; about 1,050 microns or less; about 1,040 microns or less; about 1,030 microns or less; about 1,020 microns or less; about 1,010 microns or less; about 1,000 microns or less; about 900 microns or less; about 700 microns or less; about 500 microns or less; about 400 microns or less; about 300 microns or less; about 100 microns or less) and/or about 10 microns or more (e.g., about 100 microns or more; about 300 microns or more; about 400 microns or more; about 500 microns or more; about 700 microns or more; about 900 microns or more; about 1,000 microns or more; about 1,010 microns or more; about 1,020 microns or more; about 1,030 microns or more; about 1,040 microns or more; about 1,050 microns or more; about 1,060 microns or more; about 1,070 microns or more; about 1,080 microns or more; about 1,090 microns or more; about 1,100 microns or more; about 1,150 microns or more; about 1,200 microns or more; about 1,500 microns or more; about 2,000 microns or more; about 2,500 microns or more). In some embodiments, particle 100 can have a diameter of less than about 100 microns (e.g., less than about 50 microns).

In some embodiments, particle 100 can be substantially spherical. In certain embodiments, particle 100 can have a sphericity of about 0.8 or more (e.g., about 0.85 or more, about 0.9 or more, about 0.95 or more, about 0.97 or more). Particle 100 can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more). The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as Da/Dp (where $Da=\sqrt{(4A/\pi)}$; $Dp=P/\pi$; A =pixel area; P=pixel perimeter), is a value from zero to one, with one representing a perfect circle.

Particle 100 can include one or more of the block copolymers described above. In some embodiments, particle 100 can include multiple (e.g., two, three, four, five, six, seven, eight, nine, 10) different block copolymers. For example, in some embodiments, a particle can include a blend of at least two different block copolymers. Alternatively or additionally, particle 100 can include other types of materials, such as other polymers that are not block copolymers. Examples of polymers include polyvinyl alcohols ("PVA"), polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polyolefins, polypropylenes, polymethylmethacrylates, polycaprolactones, polyglycolic acids, poly(lactic-co-glycolic) acids (e.g., poly(d-lactic-co-glycolic) acids), polysulfones, polyethersulfones, polycarbonates, nylons, silicones, linear or crosslinked polysilicones, and copolymers or mixtures thereof. In certain embodiments, particle 100 can include a highly water insoluble, high molecular weight polymer. An example of such a polymer is a high molecular weight PVA that has been acetalized. Particle 100 can include substantially pure intrachain 1,3-acetalized PVA, and can be substantially free of animal derived residue such as collagen. In some embodiments, particle 100 can include a minor amount (e.g., about 2.5 weight percent or less, about one weight percent or less, about 0.2 weight percent or less) of a gelling material (e.g., a polysaccharide, such as alginate). In certain embodiments, particle 100 can include a bioabsorbable (e.g., resorbable) polymer (e.g., alginate, gelatin, albumin, resorbable polyvinyl alcohol, albumin, dextran, starch, ethyl cellulose, polyglycolic acid, polylactic acid, polylactic acid/polyglycolic acid copolymers, poly(lactic-co-glycolic) acid). Particle 100 can include, for example, polyvinyl alcohol, alginate, or both polyvinyl alcohol and alginate.

Figure 2B:
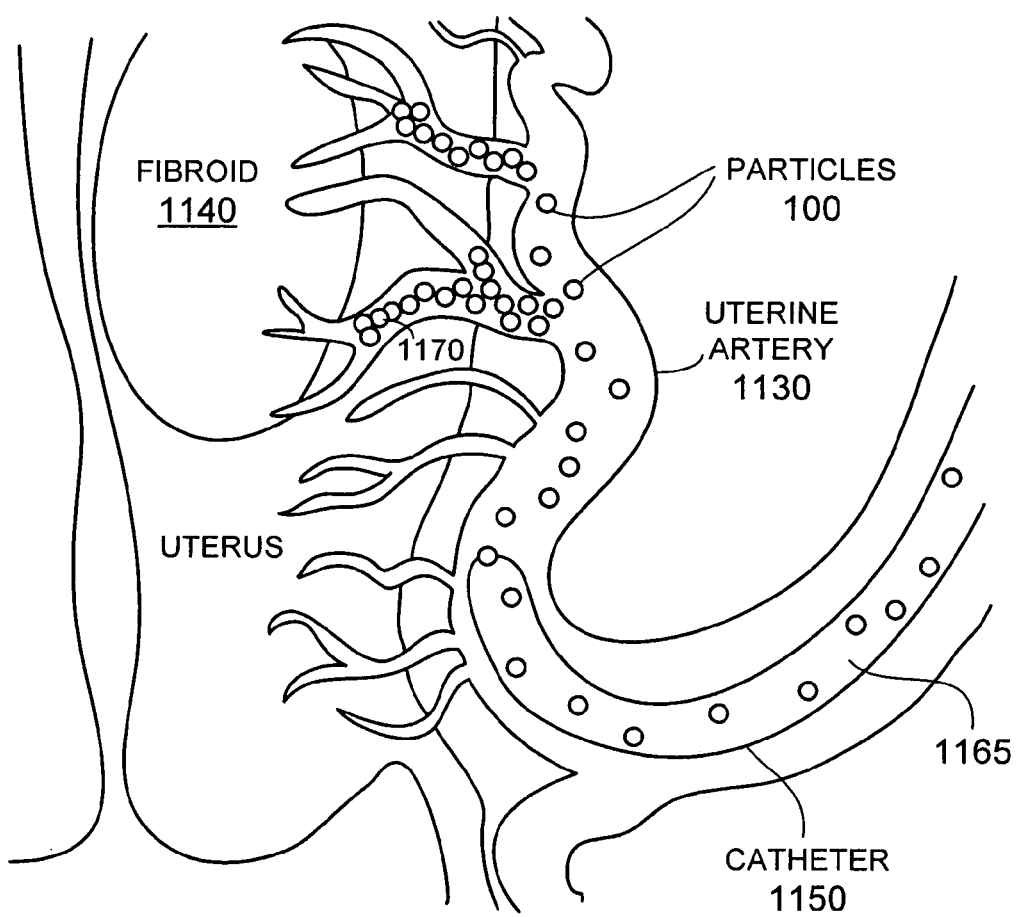
FIG. 2B is a greatly enlarged view of region 2B in FIG. 2A.

In some embodiments, in addition to or as an alternative to being used to deliver a therapeutic agent to a target site, particle 100 can be used to embolize a target site (e.g., a lumen of a subject). For example, multiple particles can be combined with a carrier fluid (e.g., a pharmaceutically acceptable carrier, such as a saline solution, a contrast agent, or both) to form a composition, which can then be delivered to a site and used to embolize the site. FIGS. 2A and 2B illustrate the use of a composition including particles to embolize a lumen of a subject. As shown, a composition, including particles 100 and a carrier fluid, is injected into a vessel through an instrument such as a catheter 1150. Catheter 1150 is connected to a syringe barrel 1110 with a plunger 1160. Catheter 1150 is inserted, for example, into a femoral artery 1120 of a subject. Catheter 1150 delivers the composition to, for example, occlude a uterine artery 1130 leading to a fibroid 1140. Fibroid 1140 is located in the uterus of a female subject. The composition is initially loaded into syringe 1110. Plunger 1160 of syringe 1110 is then compressed to deliver the composition through catheter 1150 into a lumen 1165 of uterine artery 1130.

FIG. 2B, which is an enlarged view of section 2B of FIG. 2A, shows a uterine artery 1130 that is subdivided into smaller uterine vessels 1170 (e.g., having a diameter of about two millimeters or less) which feed fibroid 1140. The particles 100 in the composition partially or totally fill the lumen of uterine artery 1130, either partially or completely occluding the lumen of the uterine artery 1130 that feeds uterine fibroid 1140.

Compositions that include particles such as particles 100 can be delivered to various sites in the body, including, for example, sites having cancerous lesions, such as the breast, prostate, lung, thyroid, or ovaries. The compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of a composition can vary based on the nature, location and severity of the condition to be treated, as well as the route of administration. A physician treating the condition, disease or disorder can determine an effective amount of composition. An effective amount of embolic composition refers to the amount sufficient to result in amelioration of symptoms and/or a prolongation of survival of the subject, or the amount sufficient to prophylactically treat a subject. The compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

A composition can include a mixture of particles (e.g., particles that include different types of block copolymers, particles that include different types of therapeutic agents), or can include particles that are all of the same type. In some embodiments, a composition can be prepared with a calibrated concentration of particles for ease of delivery by a physician. A physician can select a composition of a particular concentration based on, for example, the type of procedure to be performed. In certain embodiments, a physician can use a composition with a relatively high concentration of particles during one part of an embolization procedure, and a composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about 10 minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

In some embodiments, the carrier fluid of a composition can include a surfactant. The surfactant can help the particles to mix evenly in the carrier fluid and/or can decrease the likelihood of the occlusion of a delivery device (e.g., a catheter) by the particles. In certain embodiments, the surfactant can enhance delivery of the composition (e.g., by enhancing the wetting properties of the particles and facilitating the passage of the particles through a delivery device). In some embodiments, the surfactant can decrease the occurrence of air entrapment by the particles in a composition. Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, a composition can include from about 0.05 percent by weight to about one percent by weight (e.g., about 0.1 percent by weight, about 0.5 percent by weight) of a surfactant. A surfactant can be added to the carrier fluid prior to mixing with the particles and/or can be added to the particles prior to mixing with the carrier fluid.

In some embodiments, among the particles delivered to a subject (e.g., in a composition), the majority (e.g., about 50 percent or more, about 60 percent or more, about 70 percent or more, about 80 percent or more, about 90 percent or more) of the particles can have a diameter of about 3,000 microns or less (e.g., about 2,500 microns or less; about 2,000 microns or less; about 1,500 microns or less; about 1,200 microns or less; about 1,150 microns or less; about 1,100 microns or less; about 1,090 microns or less; about 1,080 microns or less; about 1,070 microns or less; about 1,060 microns or less; about 1,050 microns or less; about 1,040 microns or less; about 1,030 microns or less; about 1,020 microns or less; about 1,010 microns or less; about 1,000 microns or less; about 900 microns or less; about 700 microns or less; about 500 microns or less; about 400 microns or less; about 300 microns or less; about 100 microns or less) and/or about 10 microns or more (e.g., about 100 microns or more; about 300 microns or more; about 400 microns or more; about 500 microns or more; about 700 microns or more; about 900 microns or more; about 1,000 microns or more; about 1,010 microns or more; about 1,020 microns or more; about 1,030 microns or more; about 1,040 microns or more; about 1,050 microns or more; about 1,060 microns or more; about 1,070 microns or more; about 1,080 microns or more; about 1,090 microns or more; about 1,100 microns or more; about 1,150 microns or more; about 1,200 microns or more; about 1,500 microns or more; about 2,000 microns or more; about 2,500 microns or more). In some embodiments, among the particles delivered to a subject, the majority of the particles can have a diameter of less than about 100 microns (e.g., less than about 50 microns).

In certain embodiments, the particles delivered to a subject (e.g., in a composition) can have an arithmetic mean diameter of about 3,000 microns or less (e.g., about 2,500 microns or less; about 2,000 microns or less; about 1,500 microns or less; about 1,200 microns or less; about 1,150 microns or less; about 1,100 microns or less; about 1,090 microns or less; about 1,080 microns or less; about 1,070 microns or less; about 1,060 microns or less; about 1,050 microns or less; about 1,040 microns or less; about 1,030 microns or less; about 1,020 microns or less; about 1,010 microns or less; about 1,000 microns or less; about 900 microns or less; about 700 microns or less; about 500 microns or less; about 400 microns or less; about 300 microns or less; about 100 microns or less) and/or about 10 microns or more (e.g., about 100 microns or more; about 300 microns or more; about 400 microns or more; about 500 microns or more; about 700 microns or more; about 900 microns or more; about 1,000 microns or more; about 1,010 microns or more; about 1,020 microns or more; about 1,030 microns or more; about 1,040 microns or more; about 1,050 microns or more; about 1,060 microns or more; about 1,070 microns or more; about 1,080 microns or more; about 1,090 microns or more; about 1,100 microns or more; about 1,150 microns or more; about 1,200 microns or more; about 1,500 microns or more; about 2,000 microns or more; about 2,500 microns or more). In some embodiments, the particles delivered to a subject can have an arithmetic mean diameter of less than about 100 microns (e.g., less than about 50 microns).

Exemplary ranges for the arithmetic mean diameter of particles delivered to a subject include from about 100 microns to about 500 microns; from about 100 microns to about 300 microns; from about 300 microns to about 500 microns; from about 500 microns to about 700 microns; from about 700 microns to about 900 microns; from about 900 microns to about 1,200 microns; and from about 1,000 microns to about 1,200 microns. In general, the particles delivered to a subject (e.g., in a composition) can have an arithmetic mean diameter in approximately the middle of the range of the diameters of the individual particles, and a variance of about 20 percent or less (e.g. about 15 percent or less, about 10 percent or less).

In some embodiments, the arithmetic mean diameter of the particles delivered to a subject (e.g., in a composition) can vary depending upon the particular condition to be treated. As an example, in embodiments in which the particles are used to embolize a liver tumor, the particles delivered to the subject can have an arithmetic mean diameter of about 500 microns or less (e.g., from about 100 microns to about 300 microns; from about 300 microns to about 500 microns). As another example, in embodiments in which the particles are used to embolize a uterine fibroid, the particles delivered to the subject can have an arithmetic mean diameter of about 1,200 microns or less (e.g., from about 500 microns to about 700 microns; from about 700 microns to about 900 microns; from about 900 microns to about 1,200 microns). As an additional example, in embodiments in which the particles are used to treat a neural condition (e.g., a brain tumor) and/or head trauma (e.g., bleeding in the head), the particles delivered to the subject can have an arithmetic mean diameter of less than about 100 microns (e.g., less than about 50 microns). As a further example, in embodiments in which the particles are used to treat a lung condition, the particles delivered to the subject can have an arithmetic mean diameter of less than about 100 microns (e.g., less than about 50 microns). As another example, in embodiments in which the particles are used to treat thyroid cancer, the particles can have a diameter of about 1,200 microns or less (e.g., from about 1,000 microns to about 1,200 microns).

The arithmetic mean diameter of a group of particles can be determined using a Beckman Coulter RapidVUE Image Analyzer version 2.06 (Beckman Coulter, Miami, Fla.), described above. The arithmetic mean diameter of a group of particles (e.g., in a composition) can be determined by dividing the sum of the diameters of all of the particles in the group by the number of particles in the group.

Figure 3:
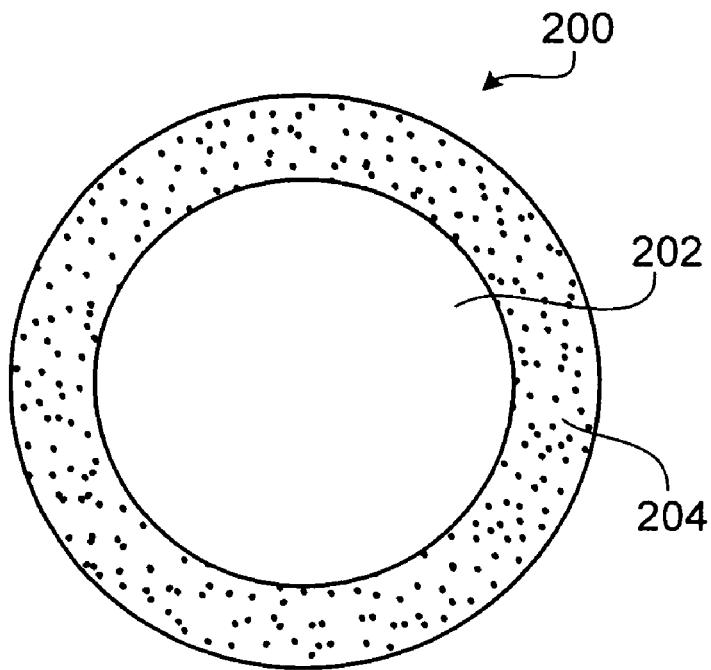
FIG. 3 is a cross-sectional view of an embodiment of a particle.

In certain embodiments, a particle that includes one of the above-described block copolymers can also include a coating. For example, FIG. 3 shows a particle 200 with an interior region 202 formed of a block copolymer, and a coating 204 formed of a different polymer (e.g., polyvinyl alcohol). Coating 204 can, for example, regulate the release of therapeutic agent from particle 200, and/or provide protection to interior region 202 of particle 200 (e.g., during delivery to a target site). In certain embodiments, coating 204 can be formed of a bioerodible and/or bioabsorbable material that can erode and/or be absorbed as particle 200 is delivered to a target site, such that interior region 202 can deliver a therapeutic agent to the target site once particle 200 has reached the target site. A bioerodible material can be, for example, a polysaccharide (e.g., alginate); a polysaccharide derivative; an inorganic, ionic salt; a water soluble polymer (e.g., polyvinyl alcohol, such as polyvinyl alcohol that has not been cross-linked); biodegradable poly DL-lactide-poly ethylene glycol (PELA); a hydrogel (e.g., polyacrylic acid, hyaluronic acid, gelatin, carboxymethyl cellulose); a polyethylene glycol (PEG); chitosan; a polyester (e.g., a polycaprolactone); a poly(ortho ester); a polyanhydride; a poly(lactic-co-glycolic) acid (e.g., a poly(d-lactic-co-glycolic) acid); a poly(lactic acid) (PLA); a poly(glycolic acid) (PGA); or a combination thereof. In some embodiments, coating 204 can be formed of a swellable material, such as a hydrogel (e.g., polyacrylamide co-acrylic acid). The swellable material can be made to swell by, for example, changes in pH, temperature, and/or salt. In embodiments in which particle 200 is used in an embolization procedure, coating 204 can swell at a target site, thereby enhancing occlusion of the target site by particle 200.

Figure 4:
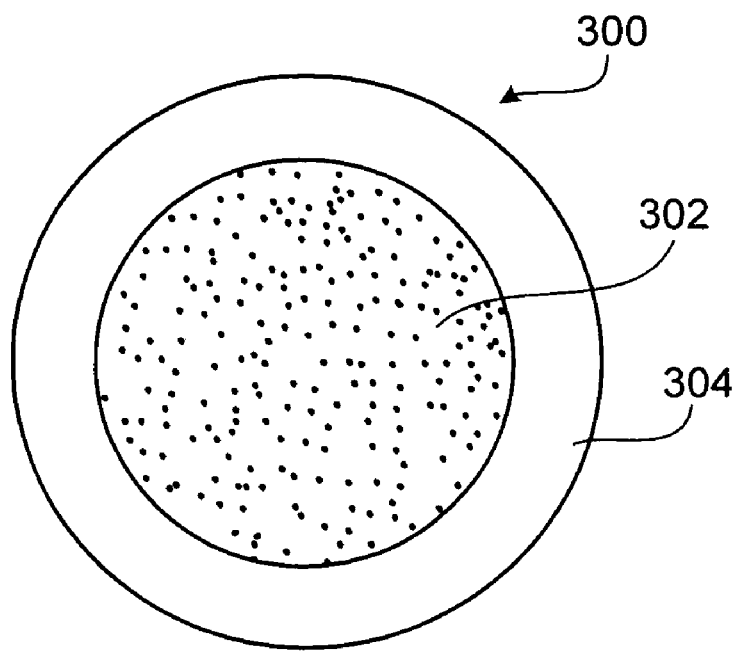
FIG. 4 is a cross-sectional view of an embodiment of a particle.

In some embodiments, a particle can include a coating that is formed of a block copolymer. For example, FIG. 4 shows a particle 300 that includes an interior region 302 formed of a polymer (e.g., polyvinyl alcohol), and a coating 304 formed of a block copolymer (e.g., SIBS). In certain embodiments, interior region 302 can be formed of a swellable material. In some such embodiments, coating 304 can be formed of a porous material. The pores in coating 304 can expose interior region 302 to changes in, for example, pH, temperature, and/or salt. When interior region 302 is exposed to these changes, the swellable material in interior region 302 can swell, thereby causing particle 300 to become enlarged. In certain embodiments, coating 304 can be made of a relatively flexible material (e.g., SIBS) that can accommodate the swelling of interior region 302. The enlargement of particle 300 can, for example, enhance occlusion during an embolization procedure.

Examples of swellable materials include hydrogels, such as polyacrylic acid, polyacrylamide co-acrylic acid, hyaluronic acid, gelatin, carboxymethyl cellulose, poly(ethylene oxide)-based polyurethane, polyaspartahydrazide, ethyleneglycoldiglycidylether (EGDGE), and polyvinyl alcohol (PVA) hydrogels. In some embodiments in which a particle includes a hydrogel, the hydrogel can be crosslinked, such that it may not dissolve when it swells. In other embodiments, the hydrogel may not be crosslinked, such that the hydrogel may dissolve when it swells.

In certain embodiments, a particle can include a coating that includes one or more therapeutic agents. In some embodiments, a particle can have a coating that includes a high concentration of one or more therapeutic agents. One or more of the therapeutic agents can also be loaded into the interior region of the particle. Thus, the surface of the particle can release an initial dosage of therapeutic agent after which the body of the particle can provide a burst release of therapeutic agent. The therapeutic agent on the surface of the particle can be the same as or different from the therapeutic agent in the body of the particle. The therapeutic agent on the surface can be applied by exposing the particle to a high concentration solution of the therapeutic agent. The therapeutic agent coated particle can include another coating over the surface the therapeutic agent (e.g., a bioerodible polymer which erodes when the particle is administered). The coating can assist in controlling the rate at which therapeutic agent is released from the particle. For example, the coating can be in the form of a porous membrane. The coating can delay an initial burst of therapeutic agent release. The coating can be applied by dipping or spraying the particle. The erodible polymer can be a polysaccharide (such as an alginate). In some embodiments, the coating can be an inorganic, ionic salt. Other erodible coatings include polysaccharide derivatives, water-soluble polymers (such as polyvinyl alcohol, e.g., that has not been cross-linked), biodegradable poly DL-lactide-poly ethylene glycol (PELA), hydrogels (e.g., polyacrylic acid, hyaluronic acid, gelatin, carboxymethyl cellulose), polyethylene glycols (PEG), chitosan, polyesters (e.g., polycaprolactones), poly(ortho esters), polyanhydrides, poly (lactic acids) (PLA), polyglycolic acids (PGA), poly(lactic-co-glycolic) acids (e.g., poly(d-lactic-co-glycolic) acids), and combinations thereof. The coating can include therapeutic agent or can be substantially free of therapeutic agent. The therapeutic agent in the coating can be the same as or different from an agent on a surface layer of the particle and/or within the particle. A polymer coating (e.g. an erodible coating) can be applied to the particle surface in embodiments in which a high concentration of therapeutic agent has not been applied to the particle surface. Coatings are described, for example, in DiMatteo et al., U.S. Patent Application Publication No. U.S. 2004/0076582 A1, published on Apr. 22, 2004, which is incorporated herein by reference.

Figure 5:
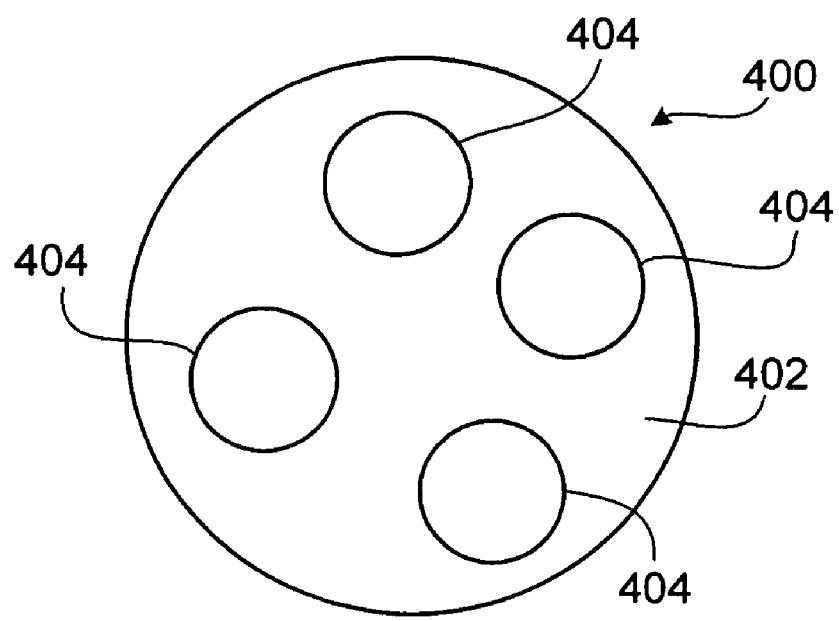
FIG. 5 is a cross-sectional view of an embodiment of a particle.

In some embodiments, a particle can include one or more smaller sub-particles. For example, FIG. 5 shows a particle 400 that includes a matrix 402, within which are embedded sub-particles 404. Matrix 402 can be formed of, for example, one or more polymers (e.g., block copolymers such as SIBS). Alternatively or additionally, sub-particles 404 can be formed of one or more polymers (e.g., block copolymers such as SIBS). In some embodiments, both matrix 402 and sub-particles 404 can be formed of one or more block copolymers. Block copolymer(s) in matrix 402 can be the same as, or different from, block copolymer(s) in sub-particles 404. In certain embodiments, particle 400 can include one or more therapeutic agents, such as water-soluble therapeutic agents and/or organic-soluble therapeutic agents. This can allow particle 400 to be used, for example, to deliver multiple therapeutic agents to a target site in one procedure. The therapeutic agents can be included in (e.g., dispersed throughout) matrix 402 and/or sub-particles 404. In some embodiments, matrix 402 can include one type of therapeutic agent (e.g., an organic-soluble therapeutic agent), while sub-particles 404 include another type of therapeutic agent (e.g., a water-soluble therapeutic agent). In certain embodiments, matrix 402 can be made out of a porous material, which can help in the release of therapeutic agent from sub-particles 404.

Examples of water-soluble therapeutic agents include DNA, oligonucleotides, heparin, urokinase, halofuginone, and protein. Examples of organic-soluble therapeutic agents include paclitaxel, trans-retinoic acid, mithramycin, probucol, rapamycin, dexamethason, 5-fluorouracil, methotrexate, doxorubicin, daunorubicin, cyclosporine, cisplatin, vinblastine, vincristine, colchicine, epothilones, endostatin, angiostatin, and plicamycin.

Figure 6A:
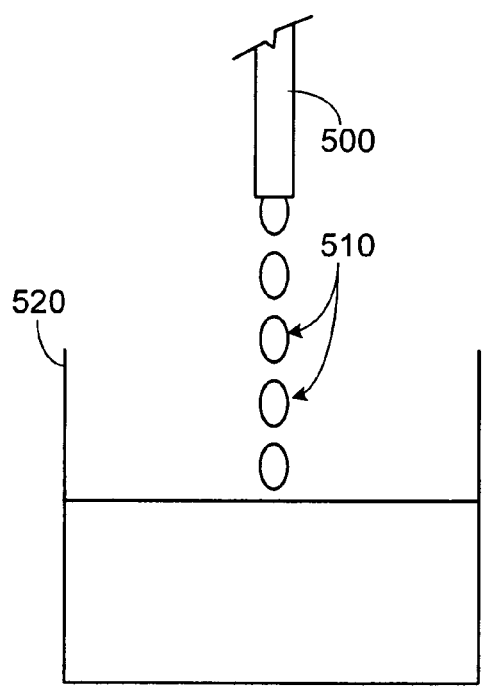
FIGS. 6A-6C are an illustration of an embodiment of a system and method for producing particles.
Figure 6B:
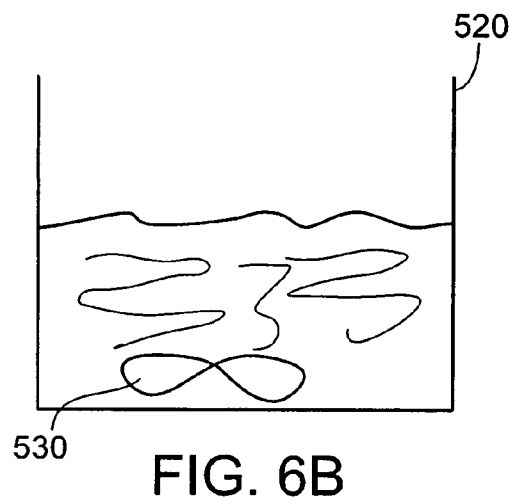
Figure 6C:
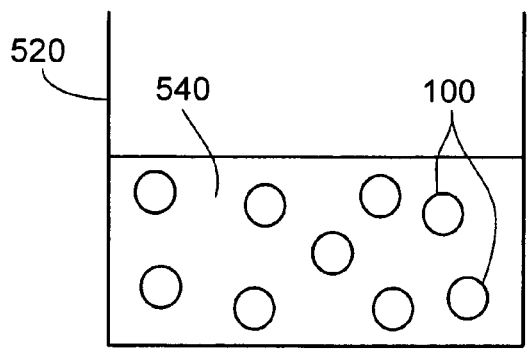

Particles can be formed by any of a number of different methods. As an example, FIGS. 6A-6C show a single-emulsion process that can be used, for example, to make particle 100 (FIG. 1). As shown in FIGS. 6A-6C, a drop generator 500 (e.g., a pipette) forms drops 510 of a solution including a block copolymer (e.g., SIBS), a therapeutic agent, and an organic solvent (e.g., methylene chloride, chloroform, tetrahydrofuran (THF), toluene). In some embodiments, the solution can include at least about one percent weight/volume (w/v) (e.g., from about one percent w/v to about 20 percent w/v) of the block copolymer. Drops 510 fall from drop generator 500 into a vessel 520 that contains an aqueous solution including a surfactant. In some embodiments, the surfactant can be water-soluble. Examples of surfactants include polyvinyl alcohols, poly(vinyl pyrrolidone) (PVP), and polysorbates (e.g., Tween® 20, Tween® 80). In certain embodiments, the aqueous solution can be mixed (e.g., homogenized) while drops 510 are being added to it. In some embodiments, the aqueous solution can be mixed at a speed of at most about 10,000 revolutions per minute (e.g., at most about 5,000 revolutions per minute, at most about 1,500 revolutions per minute). The concentration of the surfactant in the aqueous solution can be at least 0.05 percent w/v (e.g., from 0.05 percent w/v to about 10 percent w/v). In general, as the concentration of surfactant in the aqueous solution increases, particle size can decrease.

As FIG. 6B shows, after drops 510 have fallen into vessel 520, the solution is mixed using a stirrer 530. In some embodiments, the solution can be mixed (e.g., homogenized) at a speed of at least about 1,000 revolutions per minute (e.g., at least about 2,500 revolutions per minute, at least about 5,000 revolutions per minute, at least about 6,000 revolutions per minute, at least about 7,500 revolutions per minute) and/or at most about 10,000 revolutions per minute (e.g., at most about 7,500 revolutions per minute, at most about 6,000 revolutions per minute, at most about 5,000 revolutions per minute, at most about 2,500 revolutions per minute). For example, the solution can be mixed at a speed of from about 1000 revolutions per minute to about 6000 revolutions per minute. In certain embodiments, as mixing (e.g., homogenization) speed increases, particle size can decrease. In some embodiments, the solution can be mixed for a period of at least about 0.5 hour (e.g., at least about one hour, at least about two hours, at least about three hours, at least about four hours) and/or at most about five hours (e.g., at most about four hours, at most about three hours, at most about two hours, at most about one hour). In certain embodiments, the solution can be mixed for a period of from about one hour to about three hours (e.g., for about one hour). In some embodiments, mixing can occur at a temperature of at least about 25° C. (e.g., at least about 30° C., at least about 35° C.). In general, as mixing (e.g., homogenization) temperature increases, particle size can increase. The mixing results in a suspension 540 that includes particles 100 suspended in the solvent (FIG. 6C). Particles 100 are then separated from the solvent by, for example, filtration, or centrifuging followed by removal of the supernatant. Thereafter, particles 100 are dried (e.g., by evaporation, by lyophilization, by vacuum drying).

In some embodiments, the therapeutic agent can be omitted from the above-described process, such that the particles that are produced do not include therapeutic agent. Alternatively or additionally, one or more therapeutic agents can be added to the particles (e.g., by injection) after the particles have been formed.

In certain embodiments, the particles that are formed by the above-described process can be coated (e.g., with a polymer). The coating can be added to the particles by, for example, spraying and/or dip-coating. These coating processes can be used, for example, to make particles like particle 200 (FIG. 3).

Figure 7:
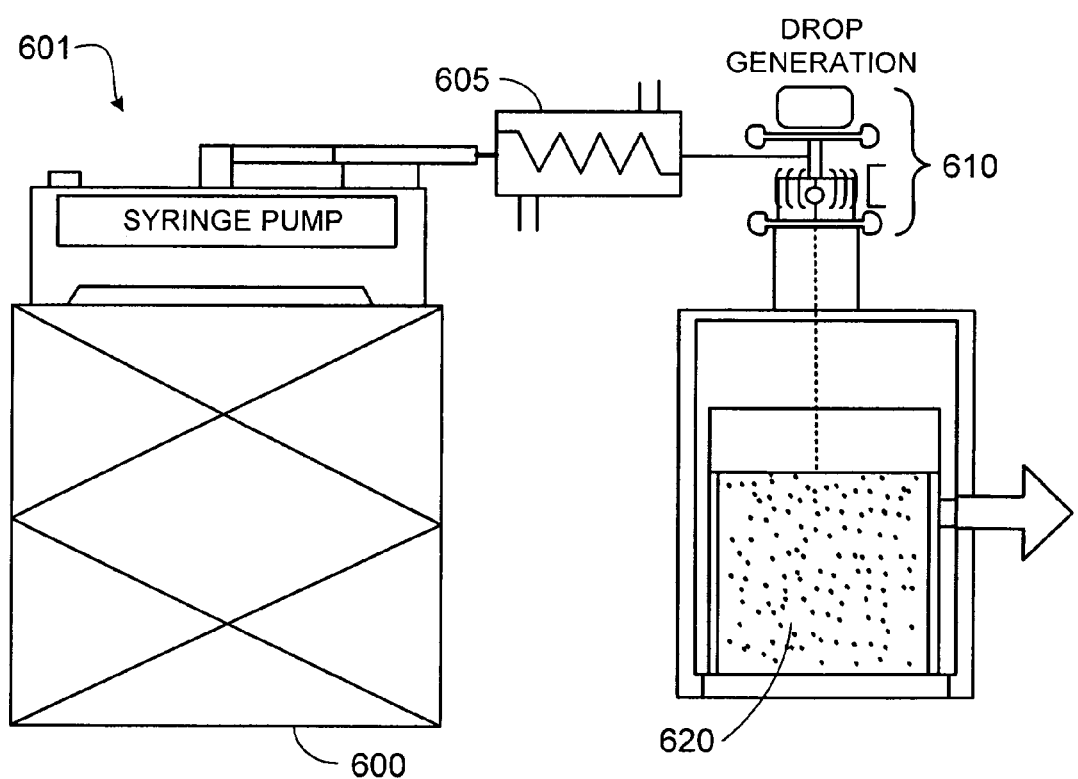
FIG. 7 is an illustration of an embodiment of a drop generator.

While a pipette has been described as an example of a drop generator that can be used in a particle formation process, in some embodiments, other types of drop generators or drop generator systems can be used in a particle formation process. For example, FIG. 7 shows a drop generator system 601 that includes a flow controller 600, a viscosity controller 605, a drop generator 610, and a vessel 620. Flow controller 600 delivers a solution (e.g., a solution that contains a block copolymer such as SIBS), a therapeutic agent, and an organic solvent) to a viscosity controller 605, which heats the solution to reduce viscosity prior to delivery to drop generator 610. The solution passes through an orifice in a nozzle in drop generator 610, forming drops of the solution. The drops are then directed into vessel 620 (e.g., containing an aqueous solution that includes a surfactant such as PVA). Drop generators are described, for example, in Lanphere et al., U.S. Patent Application Publication No. US 2004/0096662 A1, published on May 20, 2004, and in DiCarlo et al., U.S. patent application Ser. No. 11/111,511, filed on Apr. 21, 2005, and entitled "Particles", both of which are incorporated herein by reference.

Figure 8A:
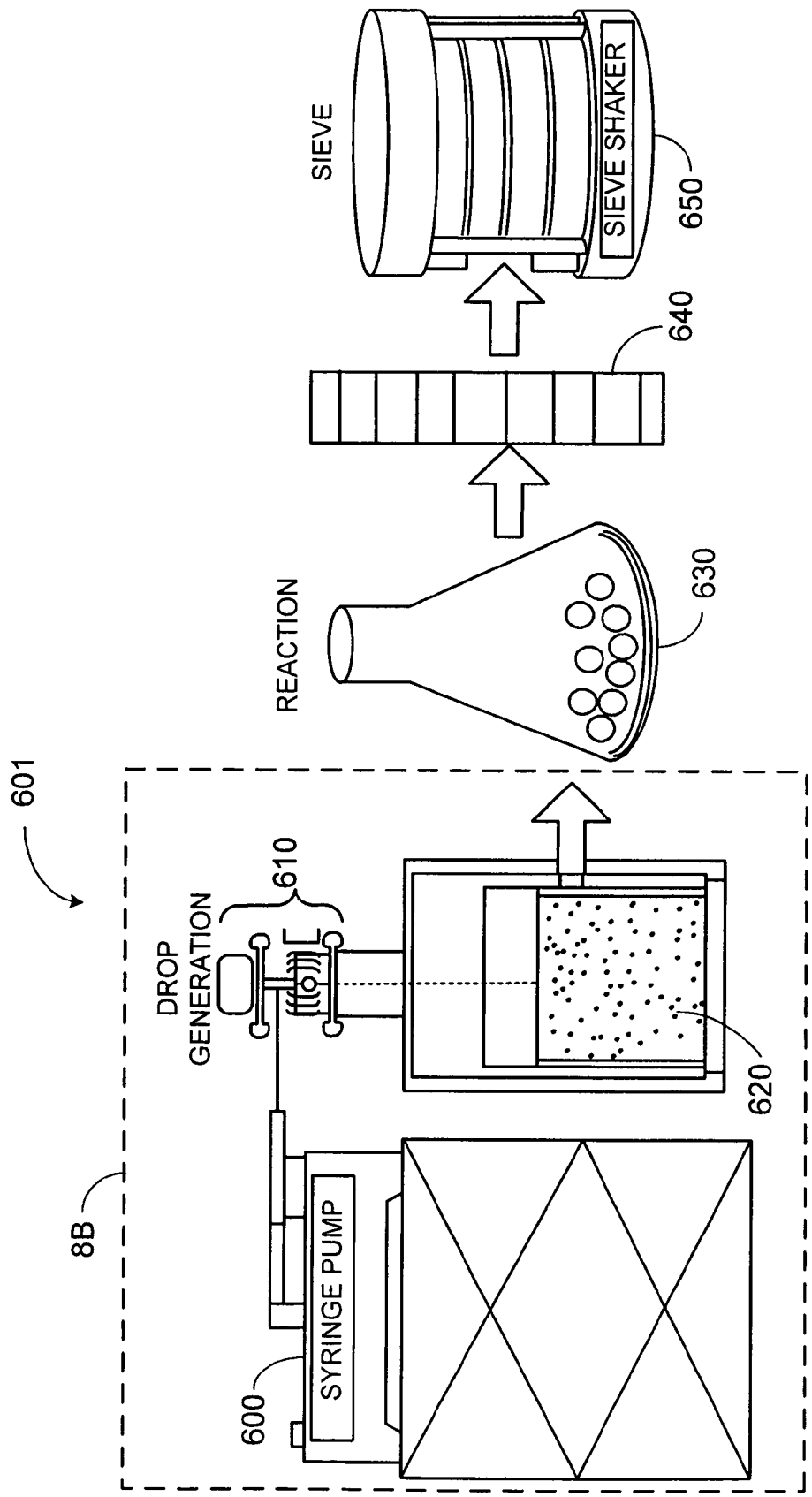
FIGS. 8A and 8B are an illustration of an embodiment of a system and method for producing particles.
Figure 8B:
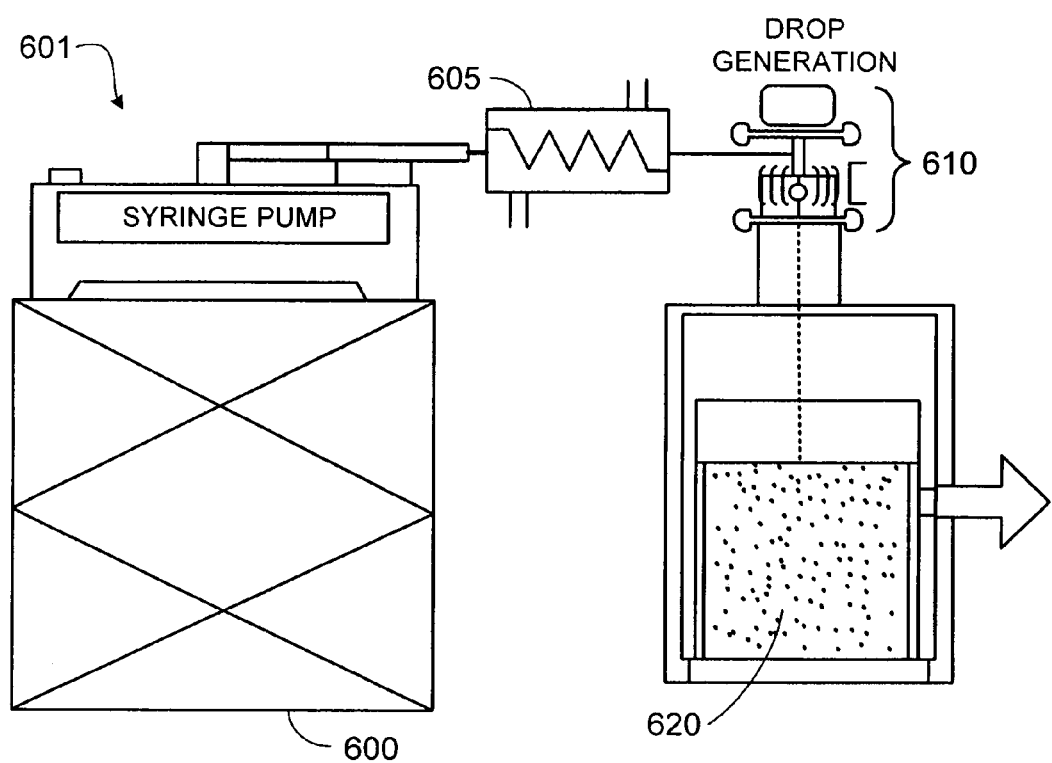

FIGS. 8A and 8B show an embodiment of a system 602 that includes drop generator system 601, and that can be used to make particles like particle 200 (FIG. 3) and particle 300 (FIG. 4). System 602 includes a drop generator system 601, a reactor vessel 630, a gel dissolution chamber 640 and a filter 650. As shown in FIG. 8B, flow controller 600 delivers a solution that contains one or more polymers (e.g., a block copolymer) and a gelling precursor (e.g., alginate) to viscosity controller 605, which heats the solution to reduce viscosity prior to delivery to drop generator 610. The solution passes through an orifice in a nozzle in drop generator 610, forming drops of the solution. The drops are then directed into vessel 620 (in this process, used as a gelling vessel), where the drops contact a gelling agent (e.g., calcium chloride) that converts the gelling precursor from a solution form into a gel form, stabilizing the drops and forming particles. In some embodiments, the particles may be transferred from vessel 620 to reactor vessel 630, where one or more polymers in the gel-stabilized particles may be reacted (e.g., cross-linked). In certain embodiments, the particles may be transferred to gel dissolution chamber 640, where the gelling precursor (which was converted to a gel) can be removed from the particles. After they have been formed, the particles can be filtered in filter 650 to remove debris. In some embodiments, the particles may thereafter be coated with, for example, a polymer (e.g., a polyvinyl alcohol). Finally, the particles can be sterilized and packaged as, for example, an embolic composition including the particles.

While alginate has been described as a gelling precursor, other types of gelling precursors can be used. Gelling precursors include, for example, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate, such as high guluronic acid, stem-derived alginate (e.g., about 50 percent or more, about 60 percent or more guluronic acid) with a low viscosity (e.g., from about 20 centipoise to about 80 centipoise at 20° C.), which can produce a high tensile, robust gel.

As described above, in some embodiments (e:g., embodiments in which alginate is used as a gelling precursor), vessel 620 can include a gelling agent such as calcium chloride. The calcium cations in the calcium chloride have an affinity for carboxylic groups in the gelling precursor. In some embodiments, the cations complex with carboxylic groups in the gelling precursor. Without wishing to be bound by theory, it is believed that the complexing of the cations with carboxylic groups in the gelling precursor can cause different regions of the gelling precursor to be pulled closer together, causing the gelling precursor to gel. In certain embodiments, the complexing of the cations with carboxylic groups in the gelling precursor can result in encapsulation of one or more other polymers (e.g., a block copolymer) in a matrix of gelling precursor.

While calcium chloride has been described as a gelling agent, other types of gelling agents can be used. Examples of gelling agents include divalent cations such as alkali metal salts, alkaline earth metal salts, or transition metal salts that can ionically cross-link with the gelling precursor. In some embodiments, an inorganic salt, such as a calcium, barium, zinc or magnesium salt, can be used as a gelling agent.

Examples of cross-linking agents that may be used to react one or more of the polymers (e.g., polyvinyl alcohol) in reactor vessel 630 include one or more aldehydes (e.g., formaldehyde, glyoxal, benzaldehyde, aterephthalaldehyde, succinaldehyde, glutaraldehyde) in combination with one or more acids, such as relatively strong acids (e.g., sulfuric acid, hydrochloric acid, nitric acid) and/or relatively weak acids (e.g., acetic acid, formic acid, phosphoric acid).

In certain embodiments, it can be desirable to reduce the surface tension of the mixture contained in vessel 620 (e.g., when forming particles having a diameter of about 500 microns or less). This can be achieved, for example, by heating the mixture in vessel 620 (e.g., to a temperature greater than room temperature, such as a temperature of about 30° C. or more), by bubbling a gas (e.g., air, nitrogen, argon, krypton, helium, neon) through the mixture contained in vessel 620, by stirring (e.g., via a magnetic stirrer) the mixture contained in vessel 620, by including a surfactant in the mixture containing the gelling agent, and/or by forming a mist containing the gelling agent above the mixture contained in vessel 620 (e.g., to reduce the formation of tails and/or enhance the sphericity of the particles).

In certain embodiments, particles can be formed by omitting one or more of the steps from the process described with reference to FIGS. 8A and 8B. For example, one or more of the polymers may not be crosslinked, and/or the gelling precursor may not be removed.

As an additional example, FIGS. 9A-9F show a double-emulsion process that can be used, for example, to make particles that, like particle 400 (FIG. 5), include sub-particles.

Figure 9A:
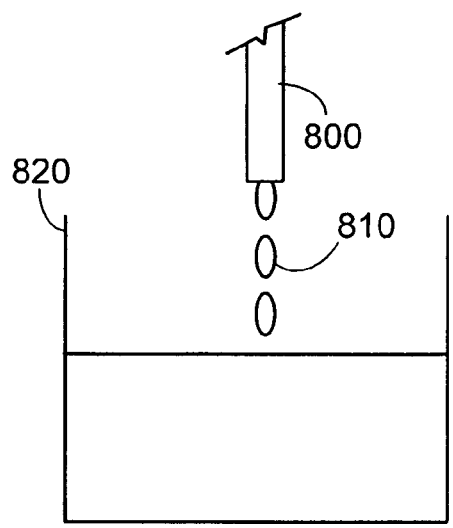
FIGS. 9A-9F are an illustration of an embodiment of a system for producing particles.
Figure 9B:
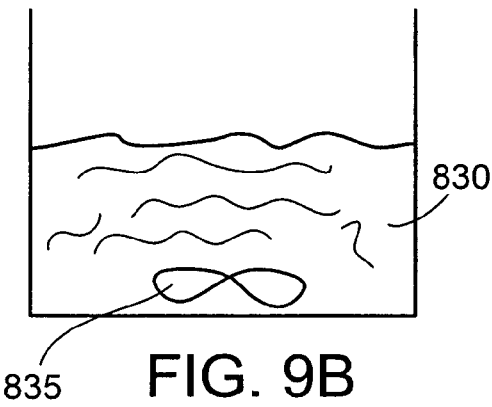
Figure 9C:
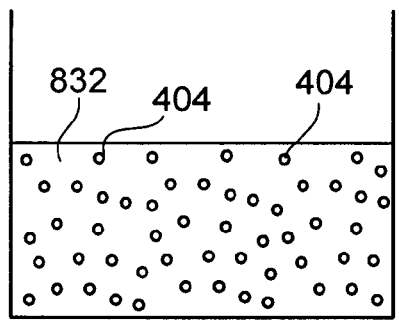
Figure 9D:
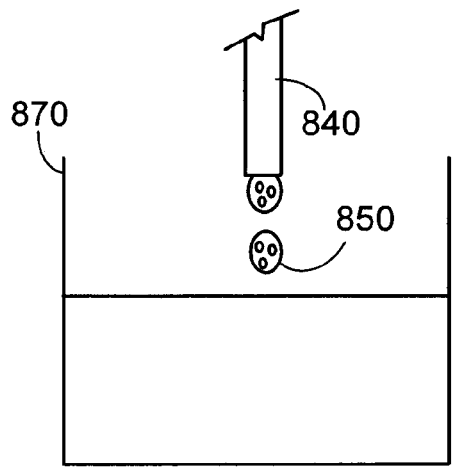

First, drop generator 800 (e.g., a pipette) forms drops 810 of an aqueous solution containing a water-soluble therapeutic agent (e.g., DNA) and a surfactant. In some embodiments, the surfactant can be water-soluble. Examples of surfactants include polyvinyl alcohols, poly(vinyl pyrrolidone) (PVP), and polysorbates (e.g., Tween® 20, Tween® 80). Drops 810 fall into a vessel 820 that includes a solution of a block copolymer (e.g., SIBS) and an organic-soluble therapeutic agent (e.g., paclitaxel) dissolved in an organic solvent, forming a mixture 830. As shown in FIG. 9B, mixture 830 is then mixed (e.g., homogenized) using a stirrer 835, to produce a suspension 832 that includes sub-particles 404 suspended in solvent (FIG. 9C). Mixing of mixture 830 can occur at a speed of, for example, at least about 5,000 revolutions per minute (e.g., at least about 7,500 revolutions per minute) and/or at most about 10,000 revolutions per minute (e.g., at most about 7,500 revolutions per minute). In some embodiments, mixture 830 can be mixed for a period of at least about one minute (e.g., at least about two minutes, at least about five minutes, at least about seven minutes) and/or at most about 10 minutes (e.g., at most about seven minutes, at most about five minutes, at most about two minutes). For example, mixture 830 may be mixed for a period of from about one minute to about five minutes.

Figure 9E:
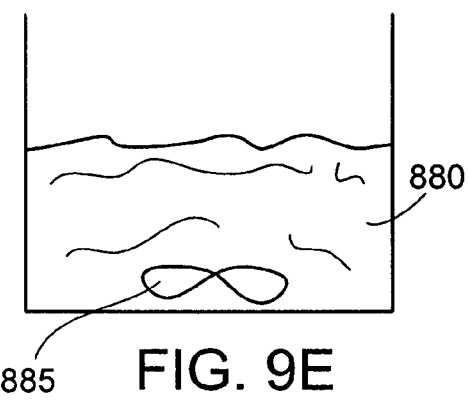
Figure 9F:
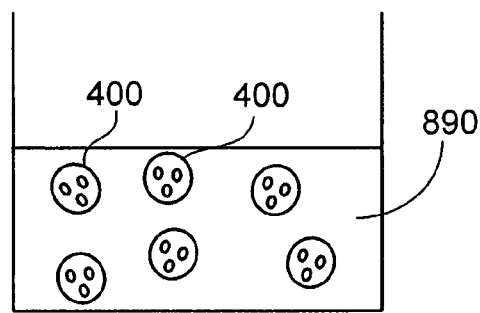
Figure 10:
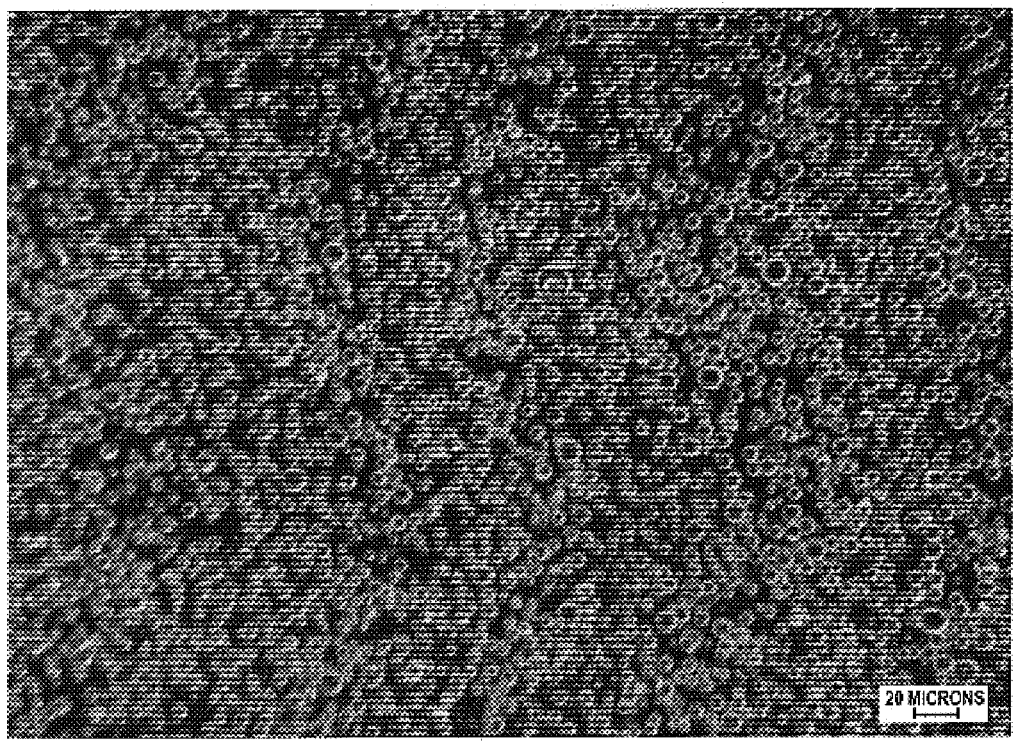
FIG. 10 is a scanning electron micrograph (SEM) image of styrene-isobutylene-styrene particles.
Figure 11:
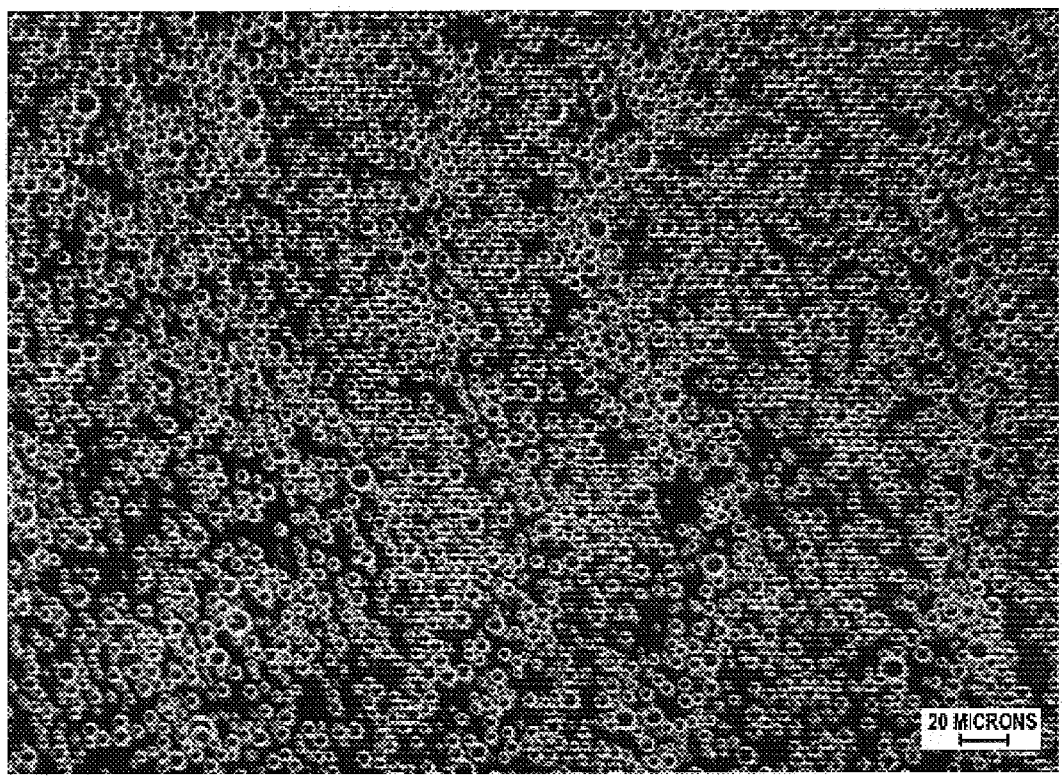
FIG. 11 is an SEM image of styrene-isobutylene-styrene particles.
Figure 12:
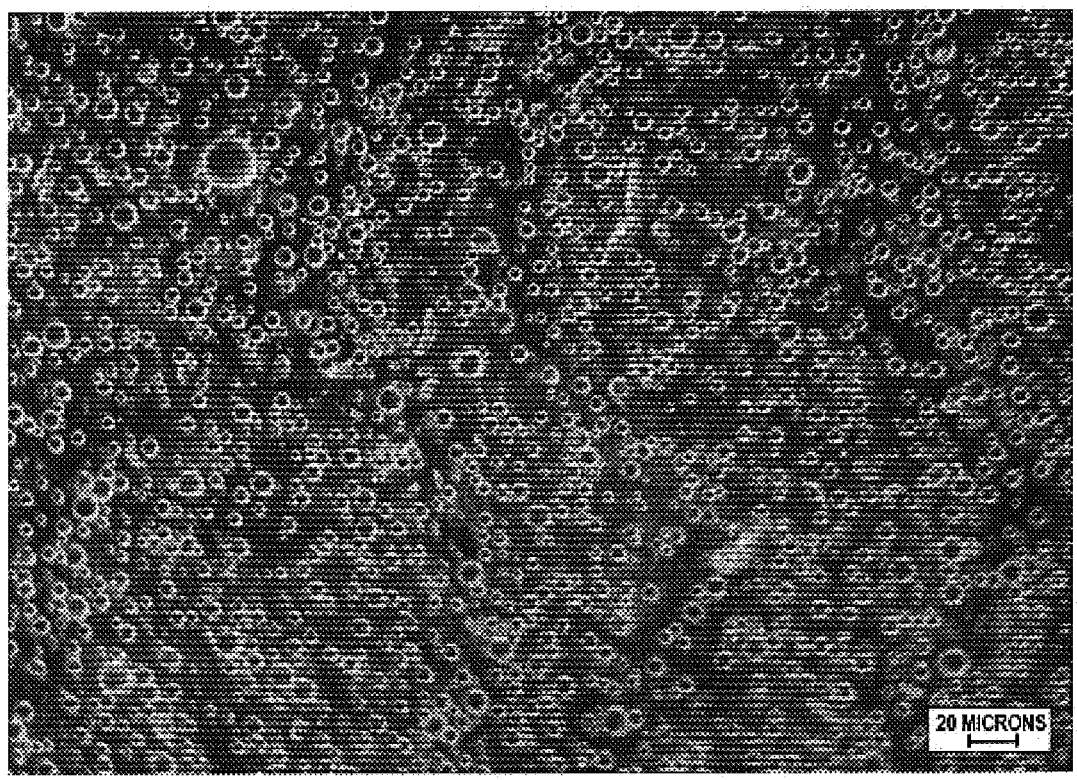
FIG. 12 is an SEM image of styrene-isobutylene-styrene particles.
Figure 13:
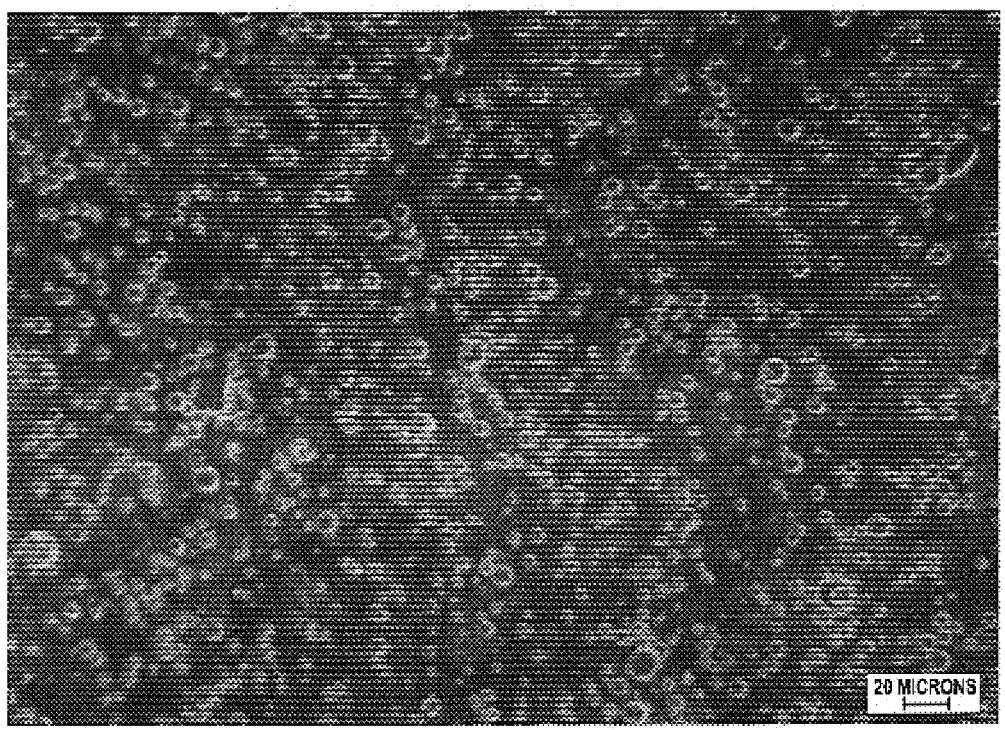
FIG. 13 is an SEM image of styrene-isobutylene-styrene particles.
Figure 14:
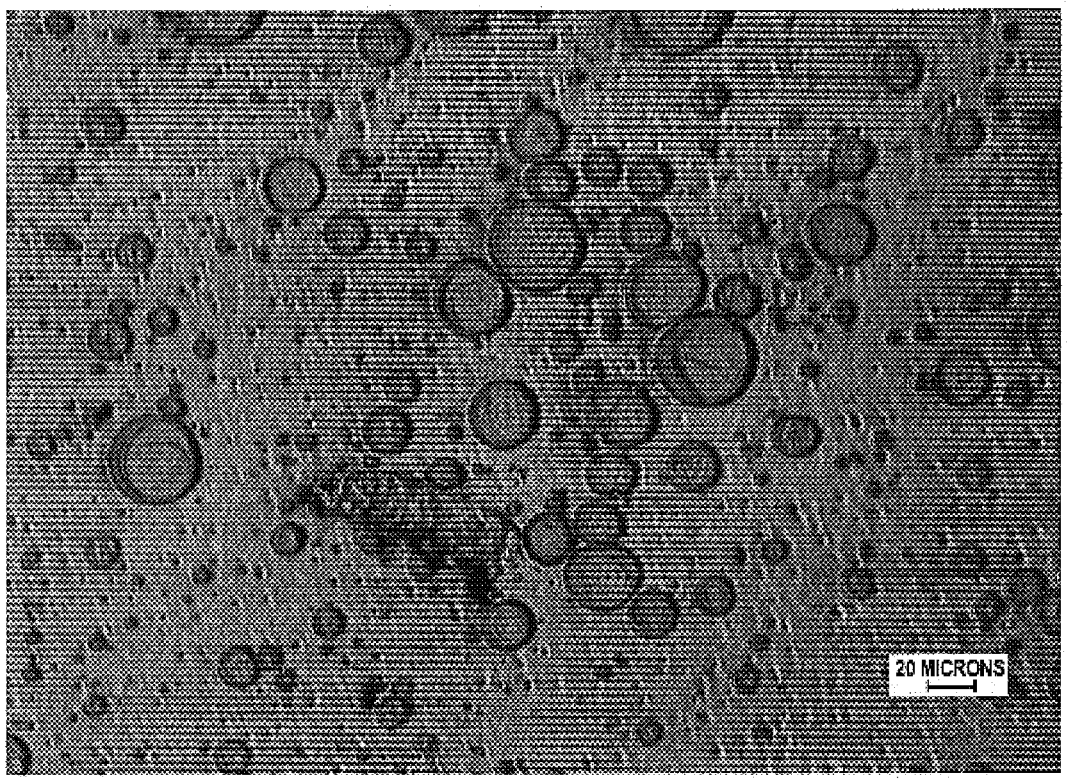
FIG. 14 is an SEM image of styrene-isobutylene-styrene particles.

After suspension 832 has been formed, suspension 832 is added to a drop generator 840 (FIG. 9D) to produce drops 850. Drops 850 fall into a vessel 870 that includes an aqueous solution, forming a mixture 880. In some embodiments, the aqueous solution in vessel 870 includes a surfactant (e.g., PVA). As FIG. 9E shows, mixture 880 is mixed (e.g., homogenized) using a stirrer 885, at a mixing speed that is lower than the speed of the first mixing. In certain embodiments, mixture 880 can be mixed at a speed of at most about 2,000 revolutions per minute (e.g., at most about 1,500 revolutions per minute, at most about 1,000 revolutions per minute, at most about 500 revolutions per minute) and/or at least about 100 revolutions per minute (e.g., at least about 500 revolutions per minute, at least about 1,000 revolutions per minute, at least about 1,500 revolutions per minute). This second mixing can last for a period of, for example, at least about one minute (e.g., at least about two minutes, at least about four minutes, at least about six minutes, at least about eight minutes, at least about 10 minutes, at least about 20 minutes, at least about 30 minutes, at least about 40 minutes, at least about 50 minutes, at least about one hour, at least about two hours, at least about four hours, at least about six hours, at least about eight hours, at least about 10 hours) and/or at most about 12 hours (e.g., at most about 10 hours, at most about 8 hours, at most about 6 hours, at most about four hours, at most about two hours, at most about one hour, at most about 50 minutes, at most about 40 minutes, at most about 30 minutes, at most about 20 minutes, at most about 10 minutes, at most about eight minutes, at most about six minutes, at most about four minutes, at most about two minutes). Mixing (e.g., homogenization) of mixture 880 produces a suspension 890 including particles 400 in solvent (FIG. 9F). Particles 400 are then separated from the solvent (e.g., by filtration) and dried (e.g., by evaporation). In some embodiments, particles 400 are separated from the solvent by evaporating the solvent.

In certain embodiments, one or more of the therapeutic agents can be omitted from the above-described process. In some embodiments, all of the therapeutic agents can be omitted from the above-described process, such that the particles that are produced do not include any therapeutic agent. Alternatively or additionally, one or more therapeutic agents can be added to the particles (e.g., by injection) after the particles have been formed.

Methods of forming particles are described in, for example, Buiser et al., U.S. Patent Application Publication No. U.S. 2003/0185896 A1, published on Oct. 2, 2003; Lanphere et al., U.S. Patent Application Publication No. US 2004/0096662 A1, published on May 20, 2004; Lanphere et al., U.S. Patent Application Publication No. US 2005/0263916 A1, published on Dec. 1, 2005, and entitled "Embolization"; and DiCarlo et al., U.S. patent application Ser. No.

11/111,511, filed on Apr. 21, 2005, and entitled "Particles", all of which are herein incorporated by reference.

EXAMPLES

The following examples are intended as illustrative and are not intended to be limiting.

Example 1

SIBS particles were prepared by a single-emulsion process as follows.

Preparation of SIBS Particles by Single Emulsion:

SIBS solutions were prepared by dissolving two grams (to form a two percent w/v solution), four grams (to form a four percent w/v solution), seven grams (to form a seven percent w/v solution), 10 grams (to form a 10 percent w/v solution), or 15 grams (to form a 15 percent w/v solution) of SIBS (60 mol percent styrene) in 100 milliliters of methylene chloride (model 27056-3, 99.9 percent HPLC grade, from Sigma).

The SIBS solutions were stirred overnight at ambient temperature in a sealed beaker at 800 revolutions per minute, using a multi-position stirrer (a model PC-171 Corning Scholar 171 stirrer) and stir bars (model 14-511-60, from Fisher).

Polyvinyl alcohol (PVA) solutions were prepared by dissolving one gram (for a 0.1 percent w/v solution), two grams (for a 0.2 percent w/v solution), five grams (for a 0.5 percent w/v solution), 10 grams (for a one percent w/v solution), 20 grams (for a two percent w/v solution), or 50 grams (for a five percent w/v solution) of polyvinyl alcohol in 1000 milliliters of distilled water. The polyvinyl alcohol was lot number P1763, from Sigma (average molecular weight: 70,000-100,000).

The PVA solutions were stirred overnight at 40° C. (samples 1-12) or 35° C. (sample 13) using a hot plate (a model PC620 hotplate from Corning).

The SIBS solutions were combined with the PVA solutions in a ratio of 1:20 SIBS:PVA, to form samples 1-13 of SIBS particles. The starting materials that were used to form each of these samples of SIBS particles are shown in Table 1. Five milliliters of each SIBS solution were added into a PVA solution by continuous dropping using a pipette, as the PVA solution was being homogenized at a full speed of about 10,000 revolutions per minute (samples 1-11 and 13) or 5,000 revolutions per minute (sample 12), using a PowerGen Models 700D homogenizer (Fisher Scientific). Once all of a SIBS solution had been added into its corresponding PVA solution, the resulting SIBS/PVA solution was homogenized at 10,000 revolutions per minute (samples 1-11 and 13) or 5,000 revolutions per minute (sample 12) at room temperature (25° C.) for about one hour.

After homogenization had been completed, SIBS particles were filtered out of each SIBS/PVA solution using a vacuum filter (a Milipore 47 mm All Glass Vacuum Filter Holder) and a filler paper of smaller than five microns (a Milipore Filter Membrane).

The SIBS particles that were filtered from each solution were then washed with distilled water, and filtered again. This wash and filtration step was repeated for a total of five times, in order to remove residual PVA from the SIBS particles.

The SIBS particles were then collected and dried by evaporation overnight at room temperature (25° C.).

Table 1 shows the SIBS solution concentration, the PVA solution concentration, and the SIBS:PVS Volume Ratio for the different samples of SIBS particles that were produced according to the above-described method.

TABLE 1

| Sample Number | SIBS Concentration (w/v) | PVA Concentration (w/v) | SIBS:PVA Volume Ratio |
|---|---|---|---|
| 1 | four percent | 0.1 percent | 1:20 |
| 2 | four percent | 0.2 percent | 1:20 |
| 3 | four percent | 0.5 percent | 1:20 |
| 4 | four percent | one percent | 1:20 |
| 5 | four percent | two percent | 1:20 |
| 6 | four percent | five percent | 1:20 |
| 7 | two percent | 0.2 percent | 1:20 |
| 8 | four percent | 0.2 percent | 1:20 |
| 9 | seven percent | 0.2 percent | 1:20 |
| 10 | 10 percent | 0.2 percent | 1:20 |
| 11 | 15 percent | 0.2 percent | 1:20 |
| 12 (5,000 rpm) | four percent | 0.2 percent | 1:20 |
| 13 (35° C.) | four percent | 0.2 percent | 1:20 |

FIGS. 10-14 are scanning electron micrograph images, at 20× magnification, of sample 1 particles, sample 2 particles, sample 4 particles, sample 5 particles, and sample 6 particles, respectively.

Figure 15:
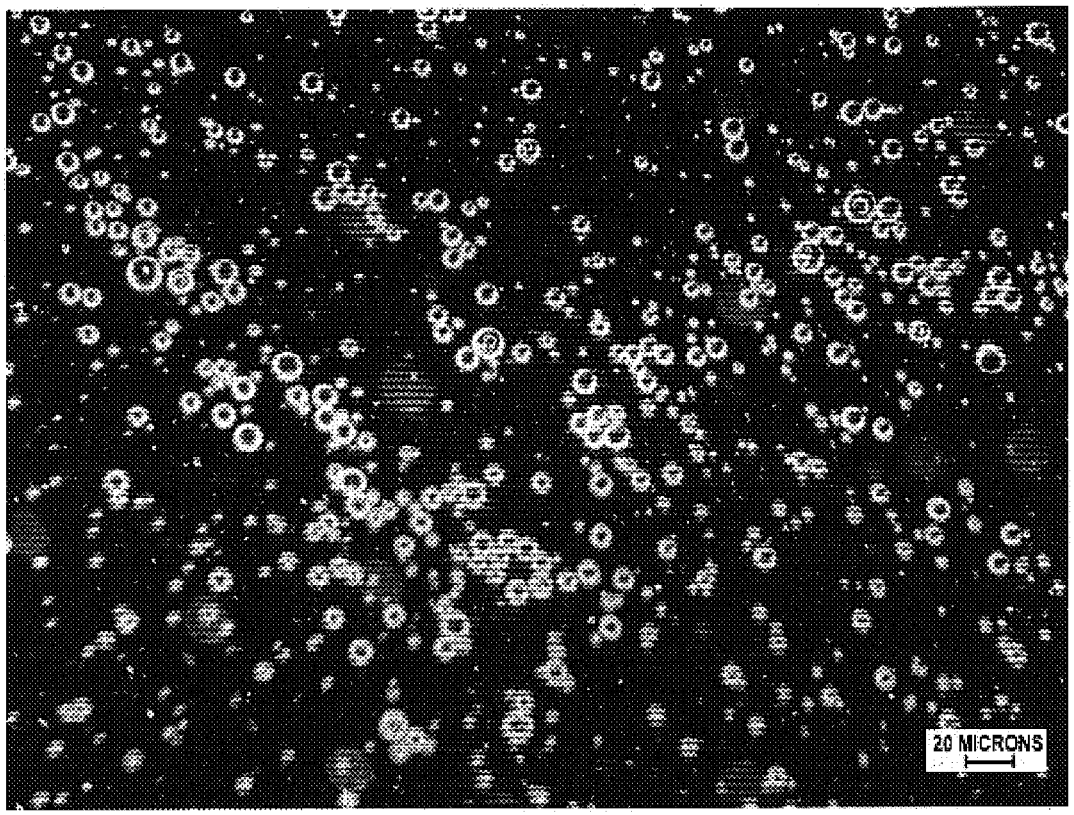
FIG. 15 is an SEM image of styrene-isobutylene-styrene particles.

FIG. 15 is a scanning electron micrograph image, at 20× magnification, of sample 12 particles, which were formed at a homogenization speed of 5,000 revolutions per minute. A comparison of the sample 12 particles of FIG. 15 with the sample 2 particles of FIG. 11 (which were formed at a homogenization speed of 10,000 revolutions per minute) indicates that homogenization speed may not have a significant effect on the sizes of the SIBS particles that are produced.

Figure 16:
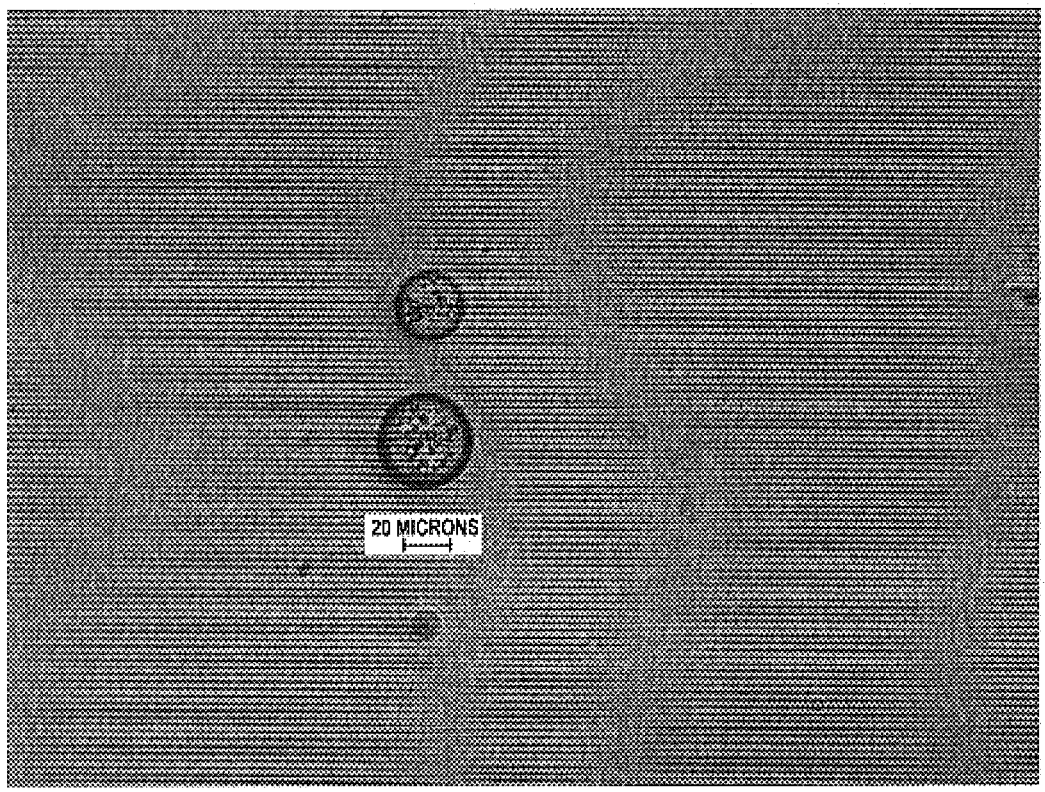
FIG. 16 is an SEM image of styrene-isobutylene-styrene particles.
Figure 17:
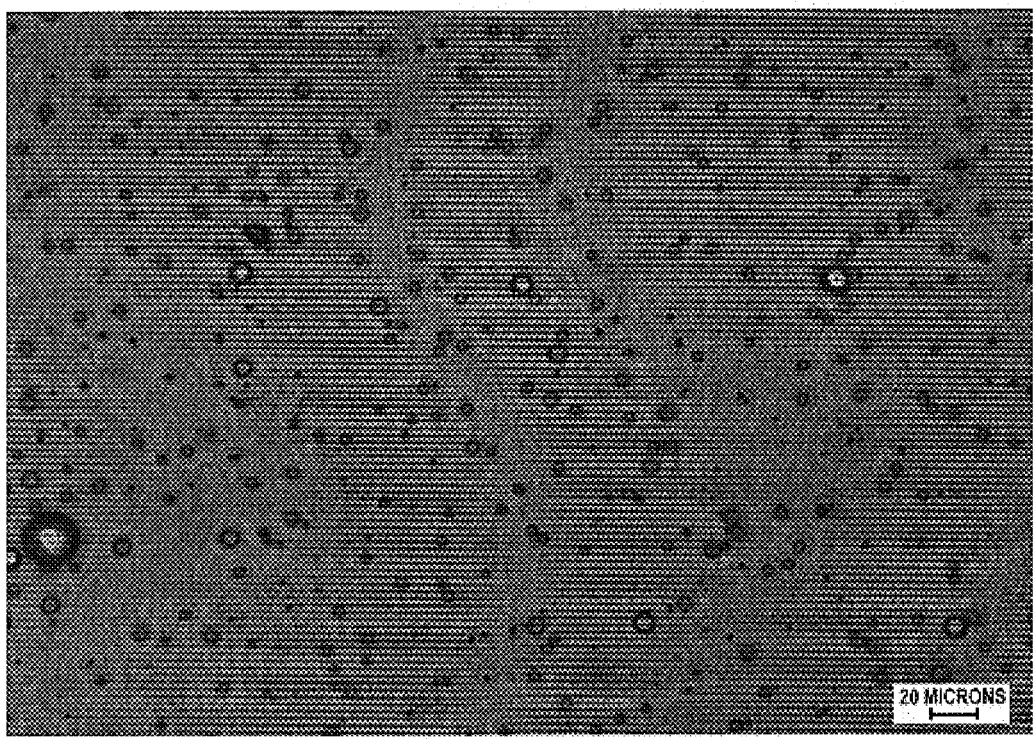
FIG. 17 is an SEM image of styrene-isobutylene-styrene particles.
Figure 18:
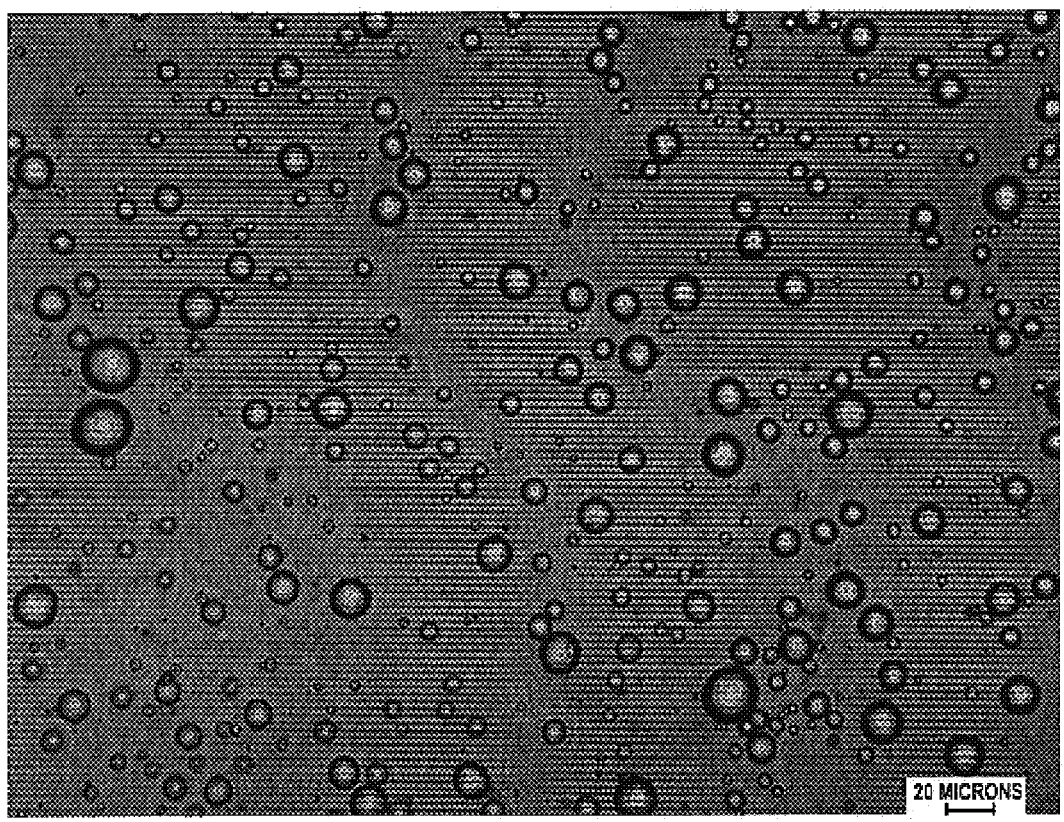
FIG. 18 is an SEM image of styrene-isobutylene-styrene particles.
Figure 19:
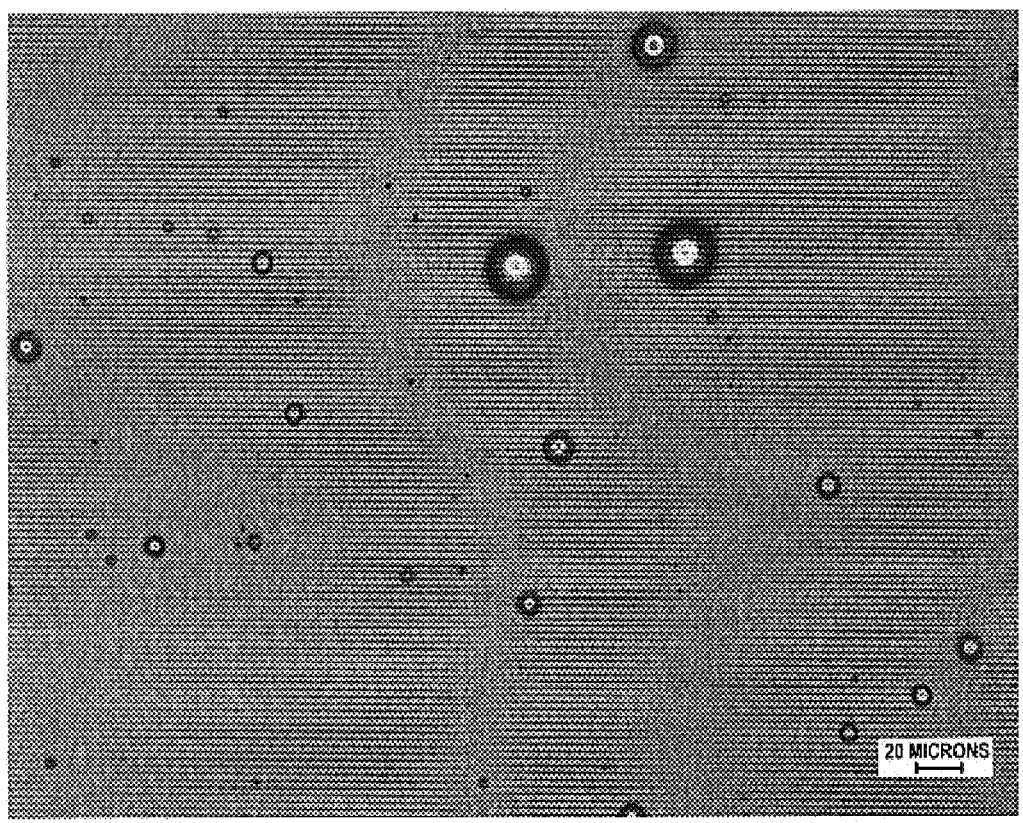
FIG. 19 is an SEM image of styrene-isobutylene-styrene particles.
Figure 20:
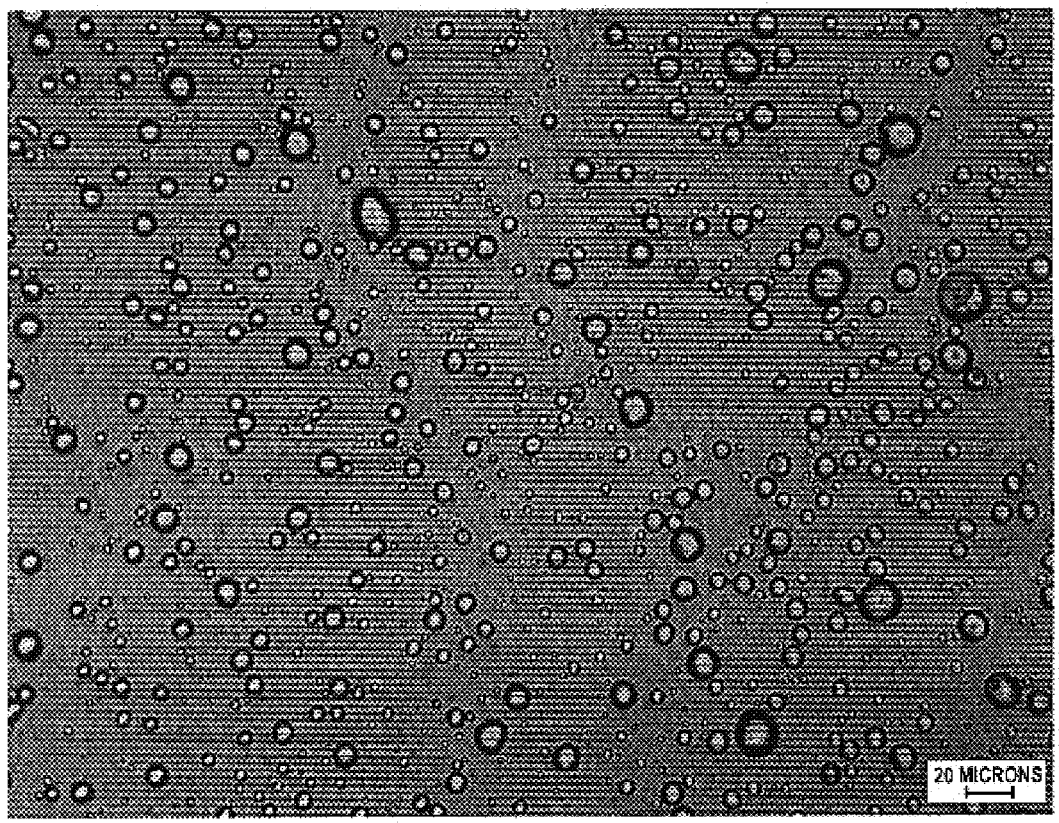
FIG. 20 is an SEM image of styrene-isobutylene-styrene particles.
Figure 21:
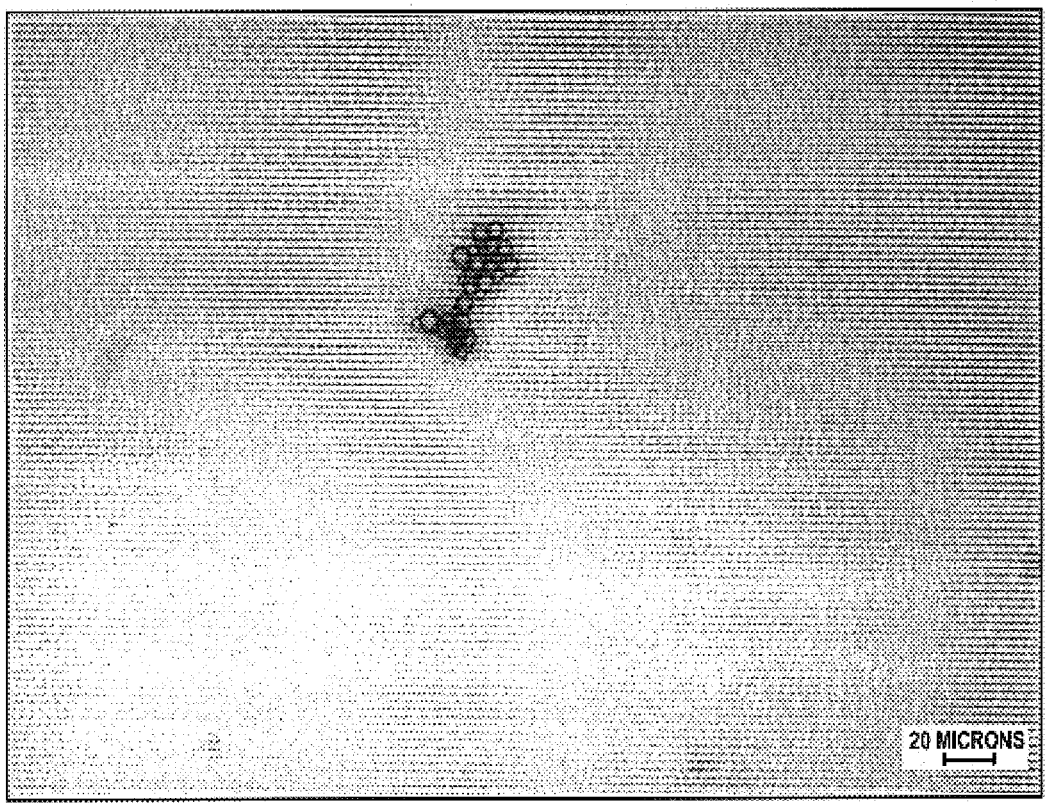
FIG. 21 is an SEM image of Rhodamine-loaded styrene-isobutylene-styrene particles.
Figure 22:
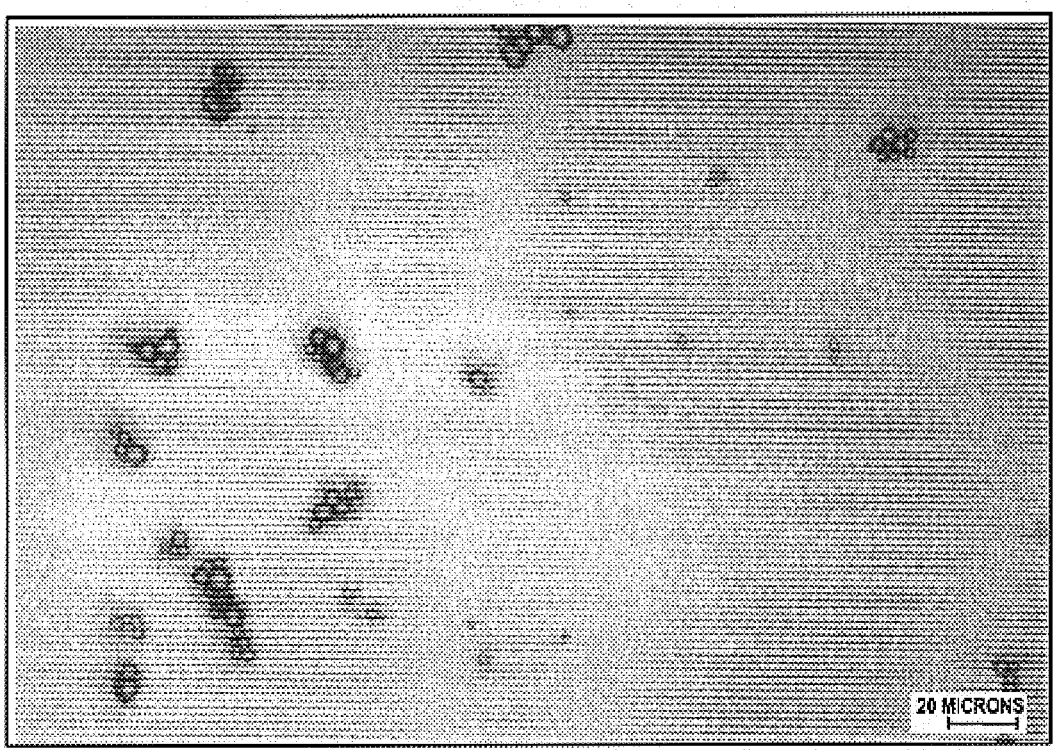
FIG. 22 is an SEM image of Rhodamine-loaded styrene-isobutylene-styrene particles.
Figure 23:
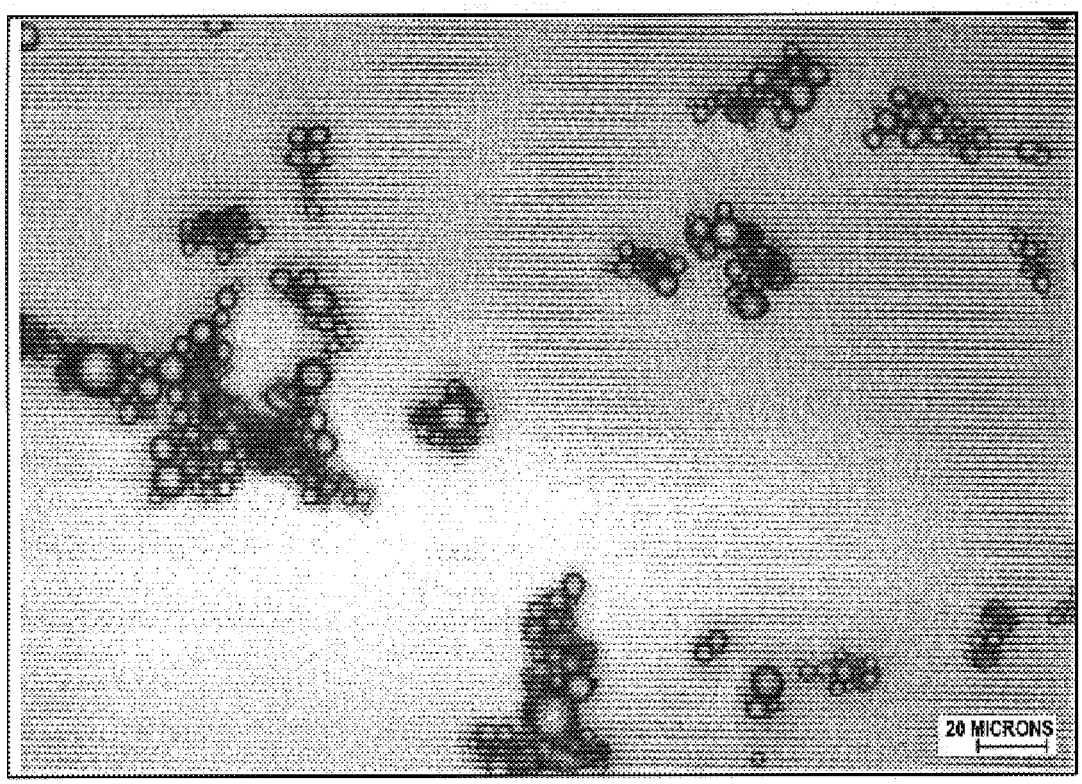
FIG. 23 is an SEM image of Rhodamine-loaded styrene-isobutylene-styrene particles.
Figure 24:
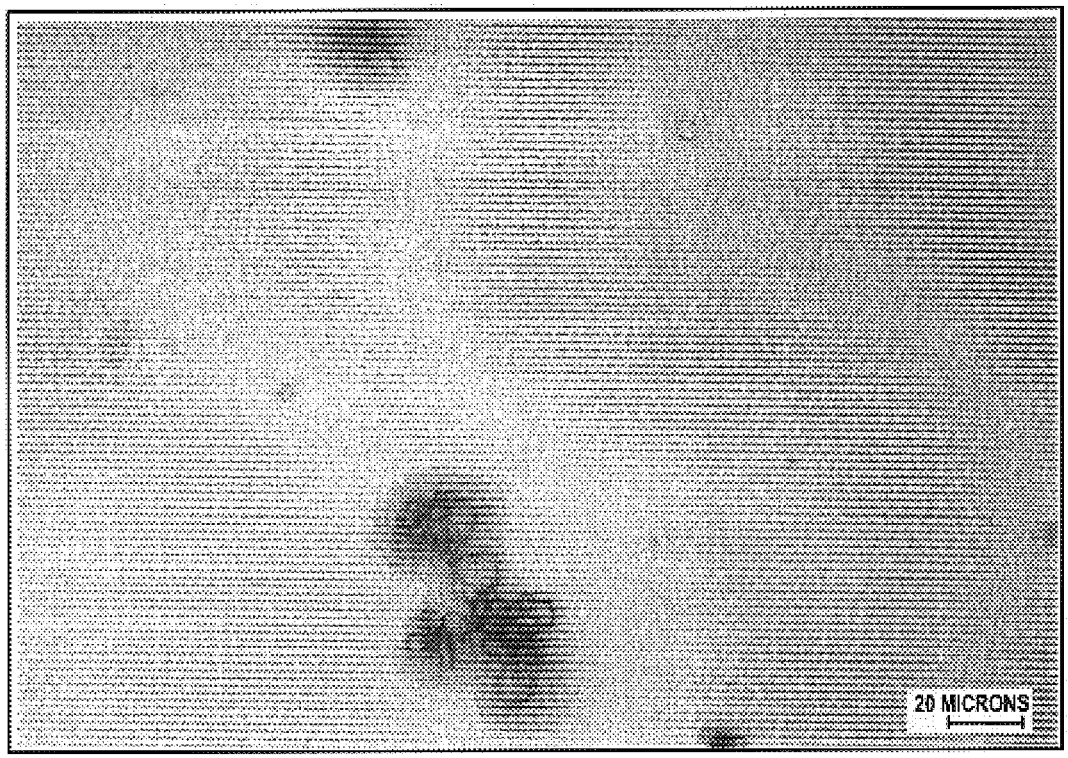
FIG. 24 is an SEM image of Rhodamine-loaded styrene-isobutylene-styrene particles.
Figure 25:
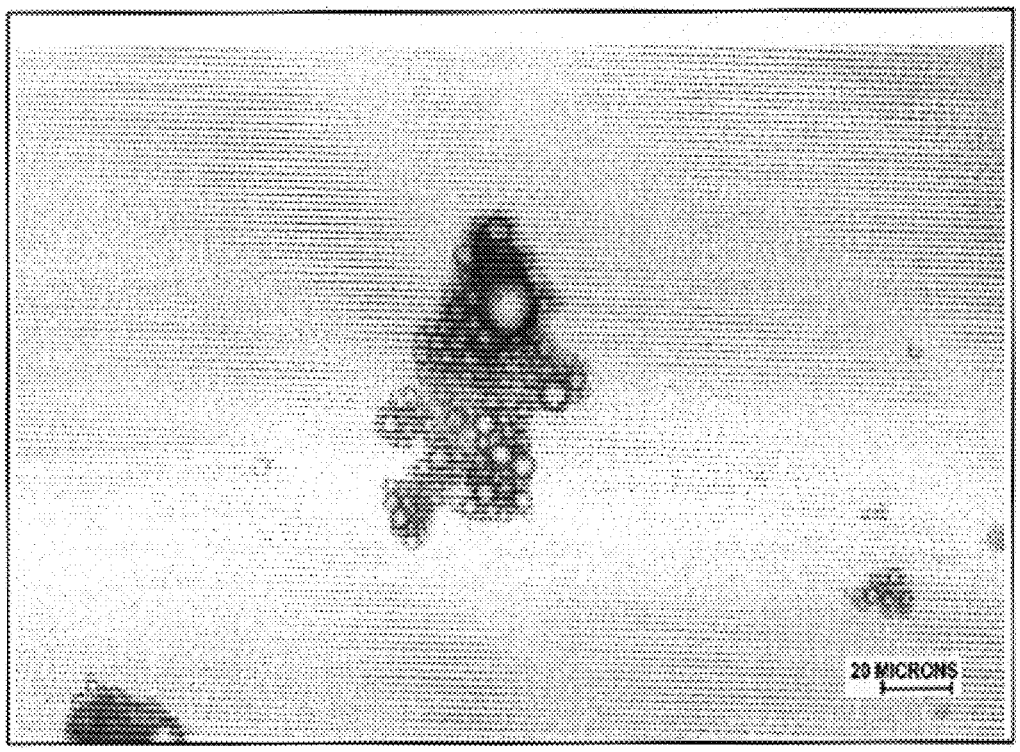
FIG. 25 is an SEM image of Rhodamine-loaded styrene-isobutylene-styrene particles.
Figure 26:
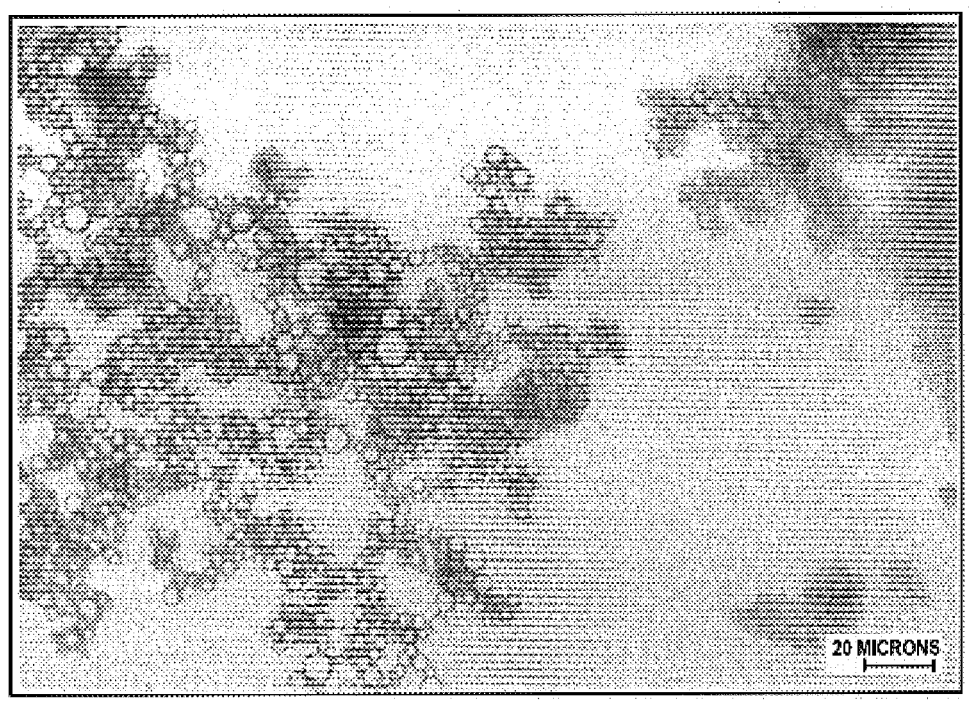
FIG. 26 is an SEM image of Rhodamine-loaded styrene-isobutylene-styrene particles.

FIG. 16 is a scanning electron micrograph image, at 20× magnification, of the sample 13 particles, which were formed at a homogenization temperature of about 35° C. A comparison of the sample 13 particles of FIG. 16 with the sample 2 particles FIG. 11 (the main difference between the two samples being the homogenization temperature) indicates that homogenization temperature may affect particle size. It appears that as the homogenization temperature increases, particle size can also increase.

FIGS. 17-20 are scanning electron micrograph images, at 20× magnification, of sample 7 particles, sample 9 particles, sample 10 particles, and sample 11 particles, respectively.

Example 2

SIBS particles including Rhodamine-B were prepared by a single-emulsion process as follows. The Rhodamine-B was used as a substitute for therapeutic agent, because it was relatively easy to determine whether the Rhodamine-B, a highly visible dye, had been incorporated into the particles. Because Rhodamine-B is soluble in organic solvents, the Rhodamine-B in this example was used as an indicator of whether an organic-soluble therapeutic agent (e.g., paclitaxel) could be incorporated into the particles.

Preparation of Rhodamine-Loaded SIBS Particles by Single Emulsion:

SIBS-Rhodamine solutions (four percent SIBS w/v) were prepared by dissolving two grams of SIBS (60 mol percent styrene) and different amounts of Rhodamine-B (10 milligrams, 100 milligrams, 200 milligrams, 300 milligrams, 400 milligrams, 1000 milligrams) in 50 milliliters of methylene chloride. The SIBS-Rhodamine solutions were stirred overnight in a sealed beaker, using a multi-position stirrer (a model PC-171 Corning Scholar 171 stirrer) and stir bars (model 14-511-60, from Fisher).

PVA solutions (0.2 percent w/v) were prepared by dissolving from 0.2 gram of PVA in 100 milliliters of distilled water.

The PVA solutions were stirred overnight at a temperature of between 35° C. and 40° C. using a hot plate (a model PC620 hotplate from Corning).

The PVA solutions (100 milliliters) were poured into 100-milliliter beakers and homogenized at 25° C. and at full speed (10,000 revolutions per minute), using a PowerGen Models 700D homogenizer (Fisher Scientific). Five milliliters of each SIBS-Rhodamine solution were slowly added to each PVA solution using a one-milliliter pipette, and the resulting SIBS-Rhodamine-PVA mixtures were homogenized for about one hour at ambient temperature, at about 1500 revolutions per minute.

After homogenization had been completed, each SIBS-Rhodamine-PVA solution was transferred into a larger beaker and stirred for at least 24 hours at ambient temperature to allow the methylene chloride to evaporate, using a multi-position stirrer (a model PC-171 Corning Scholar 171 stirrer) and stir bars (model 14-511-60, from Fisher).

Thereafter, the resulting SIBS-Rhodamine particles were filtered through a 0.22 micron filter by vacuum filtration using a vacuum filter (a Milipore 47 mm All Glass Vacuum Filter Holder) and a filter paper of smaller than five microns (a Milipore Filter Membrane). Then, the SIBS-Rhodamine particles were lyophilized overnight using a VirTis Sentry™ lyophilizer (SP Industries, Gardiner, N.Y.), set at a temperature of −50° C. for the entirety of the lyophilization.

Table 2 shows the SIBS solution concentration, the PVA solution concentration, the SIBS-Rhodamine:PVA volume ratio, and the amount of Rhodamine-B used for the different samples of SIBS-Rhodamine particles that were produced according to the above-described method.

TABLE 2

| Sample Number | SIBS Concentration (w/v) | PVA Concentration (w/v) | SIBS-Rhodamine:PVA Volume Ratio | Amount of Rhodamine Added |
|---|---|---|---|---|
| 14 | four percent | 0.2 percent | 1:20 | 10 milligrams |
| 15 | four percent | 0.2 percent | 1:20 | 100 milligrams |
| 16 | four percent | 0.2 percent | 1:20 | 200 milligrams |
| 17 | four percent | 0.2 percent | 1:20 | 300 milligrams |
| 18 | four percent | 0.2 percent | 1:20 | 400 milligrams |
| 19 | four percent | 0.2 percent | 1:20 | 1000 milligrams |

FIGS. 21-26 show sample 14 particles, sample 15 particles, sample 16 particles, sample 17 particles, sample 18 particles, and sample 19 particles, respectively.

All of the SIBS-Rhodamine particles that were prepared encapsulated the Rhodamine-B, which indicates that the particles can be used to carry a therapeutic agent.

Example 3

SIBS particles including fluorescein were prepared by a double-emulsion process as follows. The fluorescein, another highly visible dye, was used as a substitute for therapeutic agent. Because fluorescein is water-soluble, the fluorescein in this example was used as an indicator of whether a water-soluble therapeutic agent (e.g., DNA) could be incorporated into the particles.

Preparation of Fluorescein-Loaded SIBS Particles by Double Emulsion:

Five grams of SIBS (60 mol percent styrene) were dissolved in 60 milliliters of methylene chloride to form a SIBS solution.

Fifty milligrams of fluorescein and 100 milligrams of PVA were dissolved in 50 milliliters of distilled water to form a PVA-fluorescein solution.

Figure 27:
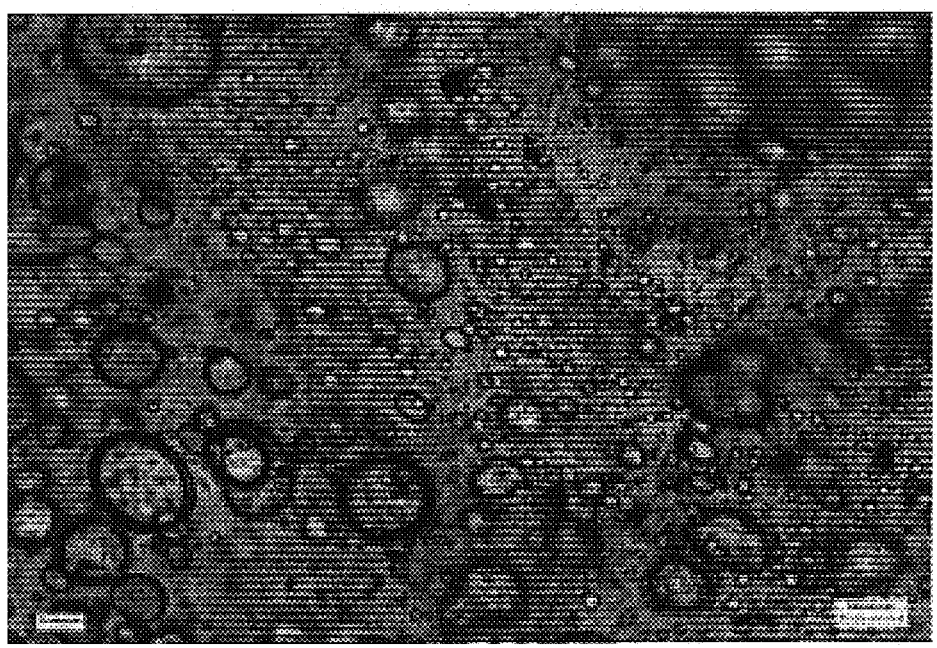
FIG. 27 is an SEM image of fluorescein-loaded styrene-isobutylene-styrene particles.

Ten milliliters of the PVA-fluorescein solution were added by pipette into 60 milliliters of the SIBS solution and homogenized for four minutes at 6000 revolutions per minute using a PowerGen Models 700D homogenizer (Fisher Scientific). The homogenization produced a SIBS-fluorescein-PVA primary emulsion which included SIBS-fluorescein primary particles. The SIBS-fluorescein primary particles are shown in FIG. 27.

Using a Pasteur pipette, the SIBS-fluorescein-PVA emulsion was then added into 540 milliliters of a 0.1 percent PVA solution (including PVA and distilled water) and homogenized at 10,000 revolutions per minute at 25° C., for a total of 90 minutes.

Figure 28:
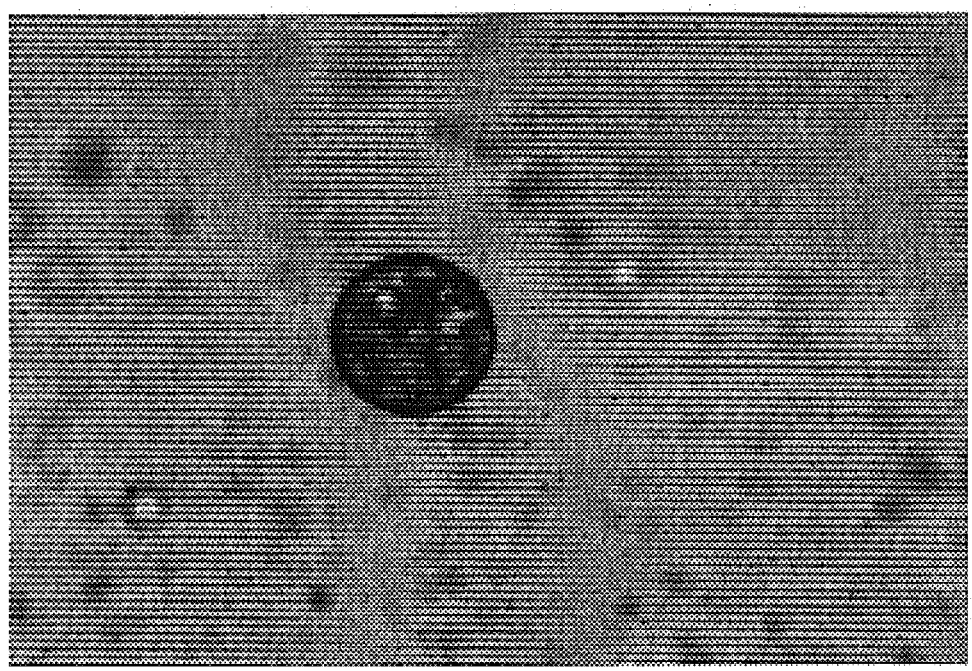
FIG. 28 is an SEM image of fluorescein-loaded styrene-isobutylene-styrene particles.

The resulting SIBS-fluorescein secondary particles were stirred for about 18 hours to harden the particles and evaporate the methylene chloride. A SIBS-fluorescein secondary particle, which includes sub-particles, is shown in FIG. 28.

Example 4

SIBS particles including fluorescein were prepared by a double vortex emulsion process as follows.

Preparation of Fluorescein-Loaded SIBS Particles by Double Vortex Emulsion:

0.5 gram of SIBS (60 mol percent styrene) was dissolved in two milliliters of methylene chloride to form a SIBS solution, and one milligram of fluorescein was dissolved in one milliliter of distilled water to form a fluorescein solution.

The SIBS solution was then vortexed for several minutes at room temperature (25° C.) using a Fisher Standard Vortex Mixer (catalog number 02-215-365) set at full speed, and 750 microliters of the fluorescein solution were added by pipette into two milliliters of the SIBS solution. The resulting mixture was vortexed for 20 seconds.

Two milliliters of a two percent PVA solution (including PVA and distilled water) were added by pipette to the mixture, and the mixture was vortexed for an additional 20 seconds.

The resulting mixture was then poured into a beaker containing 100 milliliters of a 0.2 percent PVA solution, and stirred for one minute using a multi-position stirrer (a model PC-171 Corning Scholar 171 stirrer) and stir bars (model 14-511-60, from Fisher).

Then, 100 milliliters of two percent isopropanol were added into the beaker and stirred until the methylene chloride evaporated.

Figure 29:
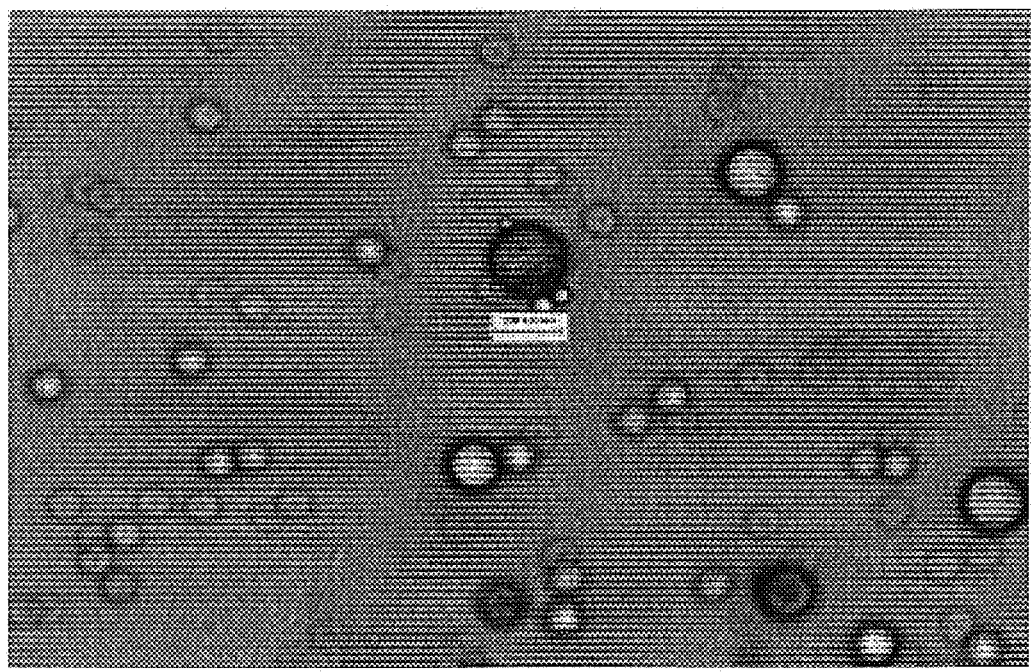
FIG. 29 is an SEM image of fluorescein-loaded styrene-isobutylene-styrene particles.

The resulting SIBS-fluorescein particles were vacuum-filtered and washed with distilled water three times. The SIBS-fluorescein particles are shown in FIG. 29.

Other Embodiments

While certain embodiments have been described, other embodiments are possible.

As an example, in certain embodiments a particle can include a block copolymer and a bioabsorbable and/or bioerodible material dispersed uniformly or non-uniformly throughout the block copolymer. The bioabsorbable and/or bioerodible material can, for example, help to delay and/or moderate therapeutic agent release from the particle.

As an additional example, in some embodiments in which a particle that includes a block copolymer is used for embolization, the particle can also include one or more other embolic agents, such as a sclerosing agent (e.g., ethanol), a liquid embolic agent (e.g., n-butyl-cyanoacrylate), and/or a fibrin agent. The other embolic agent(s) can enhance the restriction of blood flow at a target site.

As another example, in certain embodiments, a particle that includes a hydrogel can also include a coating that is formed of a bioerodible and/or bioabsorbable material. As an example, a particle can include an interior region that is formed of a hydrogel and that is coated with a coating including a bioerodible and/or bioabsorbable material. As another example, a particle can include an interior region that is coated with a hydrogel, and the hydrogel coating can further be coated with a bioerodible and/or bioabsorbable material. As an additional example, a particle can include an interior region that is formed of a hydrogel and that is coated with a block copolymer, and the block copolymer coating can further be coated with a bioerodible and/or bioabsorbable material. The presence of the bioerodible and/or bioabsorbable material in the above particles can, for example, cause a delay in the swelling of the hydrogel. In some embodiments, the hydrogel may not begin to swell until the bioerodible and/or bioabsorbable material has at least partially or completely eroded and/or been absorbed.

As a further example, in some embodiments a particle does not include any therapeutic agents.

As another example, in some embodiments a particle can be porous. In certain embodiments, a porous particle can have a substantially uniform pore structure. In some embodiments, a porous particle can have a non-uniform pore structure. For example, the particle can have a substantially non-porous interior region (e.g., formed of a polyvinyl alcohol) and a porous exterior region (e.g., formed of a mixture of a polyvinyl alcohol and alginate). Porous particles are described, for example, in Lanphere et al., U.S. Patent Application Publication No. U.S. 2004/0096662 A1, published on May 20, 2004, which is incorporated herein by reference.

As an additional example, in certain embodiments, a particle can be formed without pores (non-porous particle).

Figure 30:
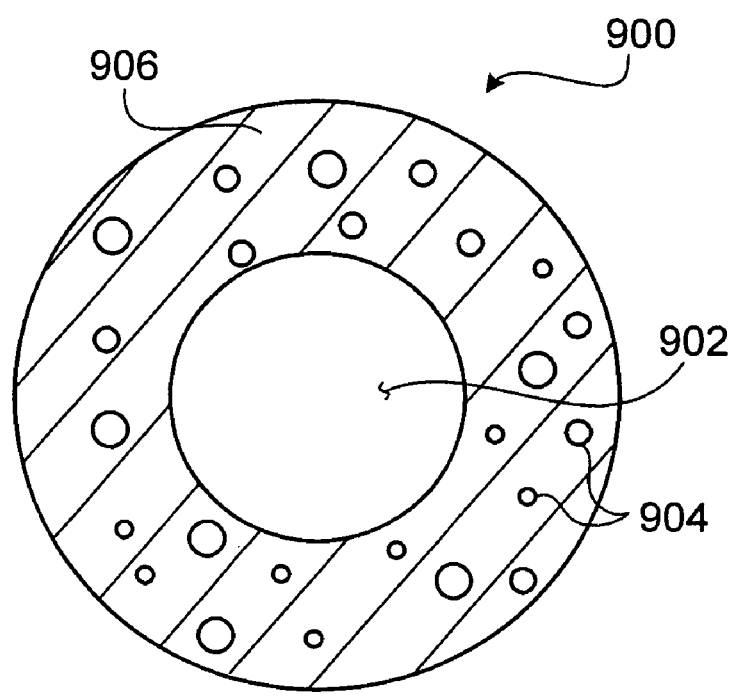
FIG. 30 is a cross-sectional view of an embodiment of a particle.

As a further example, in some embodiments, a particle (either porous or non-porous) can include at least one cavity (a hollow central region in the particle). In certain embodiments in which a particle includes a cavity, the particle can further include pores in the material surrounding the cavity. For example, FIG. 30 shows a particle 900 with a cavity 902 surrounded by a matrix material 906 (e.g., a polymer) that includes pores 904.

As another example, in some embodiments, a particle that includes a block copolymer can also include a shape memory material, which is capable of being configured to remember (e.g., to change to) a predetermined configuration or shape. In certain embodiments, particles that include a shape memory material can be selectively transitioned from a first state to a second state. For example, a heating device provided in the interior of a delivery catheter can be used to cause a particle including a shape memory material to transition from a first state to a second state. Shape memory materials and particles that include shape memory materials are described in, for example, Bell et al., U.S. Patent Application Publication No. U.S. 2004/0091543 A1, published on May 13, 2004, and DiCarlo et al., U.S. Patent Application Publication No. U.S. 2005/0095428 A1, published on May 5, 2005, both of which are incorporated herein by reference.

As an additional example, in some embodiments, a particle that includes a block copolymer can also include a surface preferential material. Surface preferential materials are described, for example, in DiCarlo et al., U.S. Patent Application Publication No. U.S. 2005/0196449 A1, published on Sep. 8, 2005, and entitled "Embolization", which is incorporated herein by reference.

As a further example, while homogenization has been described in the single-emulsion and double-emulsion processes that can be used to form particles (e.g. particles including SIBS), in some embodiments, vortexing or sonication can be used as an alternative to, or in addition to, homogenization.

As another example, in certain embodiments, particles can be linked together to form particle chains. For example, the particles can be connected to each other by links that are formed of one or more of the same material(s) as the particles, or of one or more different material(s) from the particles. Particle chains and methods of making particle chains are described, for example, in Buiser et al., U.S. Patent Application Publication No. U.S. 2005/0238870 A1, published on Oct. 27, 2005, and entitled "Embolization", which is incorporated herein by reference.

As an additional example, in some embodiments one or more particles is/are substantially nonspherical. In some embodiments, particles can be mechanically shaped during or after the particle formation process to be nonspherical (e.g., ellipsoidal). In certain embodiments, particles can be shaped (e.g., molded, compressed, punched, and/or agglomerated with other particles) at different points in the particle manufacturing process. As an example, in some embodiments in which particles include SIBS, the particles can be sufficiently flexible and/or moldable to be shaped. As another example, in certain embodiments in which particles are formed using a gelling agent, the particles can be physically deformed into a specific shape and/or size after the particles have been contacted with the gelling agent, but before the polymer(s) in the particles have been cross-linked. After shaping, the polymer(s) (e.g., polyvinyl alcohol) in the particles can be cross-linked, optionally followed by substantial removal of gelling precursor (e.g., alginate). While substantially spherical particles have been described, in some embodiments, nonspherical particles can be manufactured and formed by controlling, for example, drop formation conditions. In some embodiments, nonspherical particles can be formed by post-processing the particles (e.g., by cutting or dicing into other shapes). Particle shaping is described, for example, in Baldwin et al., U.S. Patent Application Publication No. U.S. 2003/0203985 A1, published on Oct. 30, 2003, which is incorporated herein by reference.

As a further example, in some embodiments, particles can be used for tissue bulking. As an example, the particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in Bourne et al., U.S. Patent Application Publication No. U.S. 2003/0233150 A1, published on Dec. 18, 2003, which is incorporated herein by reference.

As an additional example, in some embodiments, particles can be used in an ablation procedure. For example, the particles may include one or more ferromagnetic materials and may be used to enhance ablation at a target site. Ablation is described, for example, in Rioux et al., U.S. Patent Application Publication No. U.S. 2004/0101564 A1, published on May 27, 2004; Lanphere et al. U.S. Patent Application Publication No. U.S. 2005/0129775 A1, published on Jun. 16, 2005, and entitled "Ferromagnetic Particles and Methods"; and Lanphere et al., U.S. patent application Ser. No. 11/117, 156, filed on Apr. 28, 2005, and entitled "Tissue-Treatment Methods", all of which are incorporated herein by reference.

As another example, in some embodiments a solution can be added to the nozzle of a drop generator to enhance the porosity of particles produced by the drop generator. Examples of porosity-enhancing solutions include starch, sodium chloride at a relatively high concentration (e.g., more than about 0.9 percent, from about one percent to about five percent, from about one percent to about two percent), and calcium chloride (e.g., at a concentration of at least about 50 mM). For example, calcium chloride can be added to a sodium alginate gelling precursor solution to increase the porosity of the particles produced from the solution.

As a further example, while certain methods of making particles have been described, in some embodiments, other methods can be used to make particles. For example, in some embodiments (e.g., in some embodiments in which particles having a diameter of less than about one micron are being formed), particles can be formed using rotor/stator technology (e.g., Polytron® rotor/stator technology from Kinmatica Inc.), high-pressure homogenization (e.g., using an APV-Gaulin microfluidizer or Gaulin homogenizer), mechanical shear (e.g., using a Gifford Wood colloid mill), and/or ultrasonification (e.g., using either a probe or a flow-through cell).

As an additional example, in some embodiments, particles having different shapes, sizes, physical properties, and/or chemical properties, can be used together in an embolization procedure. The different particles can be delivered into the body of a subject in a predetermined sequence or simultaneously. In certain embodiments, mixtures of different particles can be delivered using a multi-lumen catheter and/or syringe. In some embodiments, particles having different shapes and/or sizes can be capable of interacting synergistically (e.g., by engaging or interlocking) to form a well-packed occlusion, thereby enhancing embolization. Particles with different shapes, sizes, physical properties, and/or chemical properties, and methods of embolization using such particles are described, for example, in Bell et al., U.S. Patent Application Publication No. U.S. 2004/0091543 A1, published on May 13, 2004, and in DiCarlo et al., U.S. Patent Application Publication No. U.S. 2005/0095428 A1, published on May 5, 2005, both of which are incorporated herein by reference.

Other embodiments are in the claims.

What is claimed is:

1. A particle, comprising:
a biocompatible block copolymer including at least one first block having a glass transition temperature of at most 37° C. and at least one second block having a glass transition temperature of greater than 37° C.,
wherein the at least one first block comprises at least one isobutylene monomer and the particle has a diameter that is selected from the group consisting of less than about 100 microns, from about 300 microns to about 500 microns, from about 700 microns to about 900 microns, and from about 1,000 microns to about 1,200 microns.

2. The particle of claim 1, wherein the particle has a diameter of less than about 100 microns.

3. The particle of claim 1, wherein the particle has a diameter of from about 300 microns to about 500 microns.

4. The particle of claim 1, wherein the particle has a diameter of from about 700 microns to about 900 microns.

5. The particle of claim 1, wherein the particle has a diameter of from about 1,000 microns to about 1,200 microns.

6. The particle of claim 1, wherein the at least one second block comprises at least one block selected from the group consisting of vinyl aromatic blocks, methacrylate blocks, and combinations thereof.

7. The particle of claim 1, wherein the at least one second block comprises at least one monomer selected from the group consisting of styrene, α-methylstyrene, and combinations thereof.

8. The particle of claim 1, wherein the block copolymer has the formula $X-(AB)_n$, A comprises the at least one first block, A is a isobutylene block, B comprises the at least one second block, B is a vinyl aromatic block or a methacrylate block, n is a positive whole number, and X is an initiator.

9. The particle of claim 8, wherein B is a methacrylate block.

10. The particle of claim 9, wherein B comprises at least one monomer selected from the group consisting of methylmethacrylate, ethylmethacrylate, hydroxyethyl methacrylate, and combinations thereof.

11. The particle of claim 8, wherein B is a vinyl aromatic block.

12. The particle of claim 11, wherein the at least one vinyl aromatic block comprises at least one monomer selected from the group consisting of styrene, α-methylstyrene, and combinations thereof.

13. The particle of claim 1, further comprising a therapeutic agent.

14. The particle of claim 1, wherein the block copolymer forms a coating on the particle.

15. The particle of claim 1, further comprising a bioabsorbable material.

16. The particle of claim 1, further comprising a hydrogel.

17. The particle of claim 1, wherein the block copolymer has the formula BAB or ABA, in which A is the at least one first block and B is the at least one second block.

18. The particle of claim 1, wherein the block copolymer has the formula has the formula B(AB)n or A(BA)n, in which A is the at least one first block, B is the at least one second block, and n is a positive whole number.

19. The particle of claim 1, further comprising a second polymer.

20. The particle of claim 19, wherein the second polymer is blended with the block copolymer.

21. The particle of claim 19, wherein the second polymer comprises a second block copolymer.

22. A particle, comprising:
a biocompatible block copolymer including at least one first block having a glass transition temperature of at most 37° C. and at least one second block having a glass transition temperature of greater than 37° C.,
wherein the at least one first block comprises at least one isobutylene monomer and the particle has a diameter of about 1,050 microns or more.

23. The particle of claim 22, wherein the particle has a diameter of about 1,070 microns or more.

24. The particle of claim 22, wherein the particle has a diameter of about 1,090 microns or more.

25. The particle of claim 22, wherein the particle has a diameter of about 1,100 microns or more.

26. The particle of claim 22, wherein the particle has a diameter of about 1,150 microns or more.

27. A particle, comprising:
a matrix comprising a biocompatible block copolymer including at least one first block having a glass transition temperature of at most 37° C. and at least one second block having a glass transition temperature of greater than 37° C.; and
at least one sub-particle that is at least partially disposed within the matrix,
wherein the at least one first block comprises at least one isobutylene monomer and the particle has a diameter that is selected from the group consisting of less than about 100 microns, from about 300 microns to about 500 microns, from about 700 microns to about 900 microns, and from about 1,000 microns to about 1,200 microns.

28. The particle of claim 27, wherein the at least one sub-particle comprises a plurality of sub-particles.

29. The particle of claim 27, further comprising a first therapeutic agent.

30. The particle of claim 29, further comprising a second therapeutic agent that is different from the first therapeutic agent.

31. A particle, comprising:
a matrix comprising a biocompatible block copolymer including at least one first block having a glass transition temperature of at most 37° C. and at least one second block having a glass transition temperature of greater than 37° C.; and
at least one sub-particle that is at least partially disposed within the matrix,
wherein the at least one first block comprises at least one isobutylene monomer and the particle has a diameter of about 1,050 microns or more.

32. The particle of claim 1, wherein the block copolymer comprises styrene-isobutylene-styrene.

33. The particle of claim 22, wherein the block copolymer comprises styrene-isobutylene-styrene.

34. The particle of claim 27, wherein the block copolymer comprises styrene-isobutylene-styrene.

35. The particle of claim 31, wherein the block copolymer comprises styrene-isobutylene-styrene.

* * * * *